(12) United States Patent
Saffouri

(10) Patent No.: US 12,176,082 B1
(45) Date of Patent: *Dec. 24, 2024

(54) MEDICAL INCIDENT RESPONSE AND REPORTING SYSTEM AND METHOD

(71) Applicant: Ramsey H. Saffouri, Hallandale, FL (US)

(72) Inventor: Ramsey H. Saffouri, Hallandale, FL (US)

( * ) Notice: Subject to any disclaimer, the term of this patent is extended or adjusted under 35 U.S.C. 154(b) by 303 days.

This patent is subject to a terminal disclaimer.

(21) Appl. No.: 17/893,925

(22) Filed: Aug. 23, 2022

Related U.S. Application Data

(63) Continuation-in-part of application No. 16/531,962, filed on Aug. 5, 2019, now Pat. No. 11,424,030, which is a continuation-in-part of application No. 14/696,599, filed on Apr. 27, 2015, now abandoned.

(60) Provisional application No. 61/984,231, filed on Apr. 25, 2014.

(51) Int. Cl.
| | |
|---|---|
| *G16H 10/60* | (2018.01) |
| *G16H 40/20* | (2018.01) |
| *G16H 40/67* | (2018.01) |
| *G16H 50/20* | (2018.01) |

(52) U.S. Cl.
CPC .............. *G16H 10/60* (2018.01); *G16H 40/67* (2018.01); *G16H 50/20* (2018.01); *G16H 40/20* (2018.01)

(58) Field of Classification Search
None
See application file for complete search history.

(56) References Cited

U.S. PATENT DOCUMENTS

| | | |
|---|---|---|
| 8,549,028 B1 | 10/2013 | Alon |
| 8,818,825 B1 | 8/2014 | Scorvo |
| 10,834,482 B2 | 11/2020 | Speicher |
| 11,424,030 B1 | 8/2022 | Saffouri |
| 2009/0259492 A1 | 10/2009 | Cossman |

(Continued)

OTHER PUBLICATIONS

EENA, Recording for PSAPs Future Technology, Nov. 11, 2015, Publisher: https://eena.org/document/recording-forpsaps-future-technology/.

(Continued)

*Primary Examiner* — Devin C Hein
(74) *Attorney, Agent, or Firm* — MALLOY & MALLOY, PL

(57) ABSTRACT

A medical incident response and reporting system includes a central server in communication with a contact center having a medical incident case manager communication device continuously monitored by a medical incident case manager. A patient communication device communicative with the case manager communication device to facilitate communication between the patient and the case manager to evaluate the medical incident involving the patient, while recording all communications between the patient and the case manager. A medical incident case manager communication device operative to dispatch a medical incident response specialist to the patient's location, and a medical incident response station assembly transported by the medical incident response specialist to the patient's location comprising a medical incident response station communication device also communicative with the central server to facilitate communication between at least the patient, the medical incident response specialist and the medical incident case manager from the patient's location.

16 Claims, 17 Drawing Sheets

(56) References Cited

U.S. PATENT DOCUMENTS

| | | |
|---|---|---|
| 2010/0222649 A1 | 9/2010 | Schoenberg |
| 2012/0258737 A1 | 10/2012 | Bennett, Jr. |
| 2013/0103423 A1 | 4/2013 | Kim |
| 2014/0236626 A1 | 8/2014 | Reddy Bynagari |
| 2017/0289350 A1 | 10/2017 | Philbin |

OTHER PUBLICATIONS

EENA, Public Safety Digital Transformation The Internet of Things (IOT) and Emergency Services, https://eena.org/document/the-internet-of-things-and-emergency-services/, Mar. 3, 2016.

Landman AB, Lee CH, Sasson C, Van Gelder CM, Curry LA, Prehospital Electronic Patient Care Report Systems: Early Experiences from Emergency Medical Services Agency Leaders. PLoS ONE 7(3): e32692. doi.1371/journal.pone.0032692, Jan. 1, 2012.

S. Rebecca Neusteter, Maris Mapolski, Mawai Khogali, and Megan O'toole, The 911 Call Processing System: A Review of the Literature as it Relates to Policing. New York: Vera Institute of Justice, Jan. 1, 2019.

Saver, In-Vehicle Inventory Systems Using RFID Technology Application Note, https://www.hsdl.org/?view&did=812228, Nov. 1, 2013.

Schooley B and Horan TA, Emerging Digital Technologies in Emergency Medical Services: Considerations and Strategies to Strengthen the Continuum of Care. DOT HS 811 999C. Washington, DC: National Highway Traffic Safety Administration, 2015. Available at: www.ems.gov, Aug. 1, 2015.

FIG. 6

MEDICAL INCIDENT RESPONSE AND REPORTING SYSTEM AND METHOD

CLAIM OF PRIORITY

The present application is a Continuation-In-Part (CIP) application of and claims priority to a previously filed, U.S. Non-Provisional patent application, namely, that having Ser. No. 16/531,962 and a filing date of Aug. 5, 2019, which is a Continuation-In-Part (CIP) of previously filed U.S. Non-Provisional patent application, namely, that having Ser. No. 14/696,599, and further, claims priority to a previously filed, U.S. Provisional patent application, namely, that having Ser. No. 61/984,231 and a filing date of Apr. 25, 2014, with the contents of all prior applications being incorporated herein by reference in their entireties.

BACKGROUND OF THE INVENTION

Field of the Invention

This invention is directed to a system and method for medical incident response and reporting. Specifically, at least some embodiments of the present invention are related to connecting patients and medical incident specialists, as well as for creating a comprehensive record of each medical incident and treatment regimen provided to a patient in response thereto.

Description of the Related Art

Telemedicine, telehealth, eHealth, or remote healthcare involves the use of expanding communications technology to provide clinical health care at a distance. Telemedicine eliminates distance barriers and improves access to medical services that would not otherwise be available in distant rural communities or across countries. It has also been used to save lives during emergency situations where ready access to a physician may not otherwise be available or would not be timely.

Although early forms of telemedicine were achieved via telephone and radio, they have recently been supplemented with video capability, more advanced and remote diagnostic tools such as patient monitors, sensors, and home-care devices, as well as distributed client-server applications. These advances have the potential to significantly reduce the overall cost of medical care and to increase access.

However, telemedicine still suffers from various downsides, such as the cost of telecommunication and data management, the lack of technical expertise of medical professionals who employ it, as well as an increased risk of error and exposure to liability from a lack of documentation and records of treatment. Thus, there exists a need for a system and method for telemedicine that can be implemented at a low cost, is relatively easy to use, and provides clearly documented records of the physician-patient interaction.

SUMMARY OF THE INVENTION

The present invention meets the existing needs described above by providing for a system and method for telemedicine. Accordingly, one embodiment of the present invention is directed to a system for telemedicine which may comprise a telemedicine application accessible by a patient device and a physician device. The patient device and physician device may comprise personal computers, mobile devices, wearable electronic devices, or any suitable processing device capable of accessing or executing the telemedicine application over a communication channel or network.

The telemedicine application may comprise an application server, a patient interface, a physician interface, a contact center or "triage" facility, and a recording facility. The application server may comprise a special purpose or general purpose computer structured and configured to facilitate and/or direct communications, preferably audio-visual, between at least the patient device and the physician device. Accordingly, the patient interface allows a patient to access the application server via a patient device. Similarly, the physician interface allows a patient to access the application server via a physician device.

A patient may access a patient interface in order to request medical assistance. As such, the patient interface may guide the patient through a registration process, if the patient is not already registered with the application server. The patient may be asked to provide identifying information, demographic information, current location, payment information. The patient may further be asked to sign and/or agree to various service agreements, disclaimers, waivers, or other contracts. In some embodiments, a patient may have access through a group account, such as account(s) issued to a resort facility or a hotel. The patient interface may also comprise a video module for teleconferencing with the contact center or a physician, a notification module for notifying the patient of continuity of care items, an evaluation module for providing feedback to the physician, and a medical record module for retrieving past medical history, diagnosis, and various medical data.

If a patient is already registered or otherwise has access to an account, the patient may be prompted to login, where the user may request medical assistance from a physician. In at least one embodiment, a patient, upon request for medical assistance through the patient interface, is first directed to a waiting queue until a contact personnel, which may include nonmedical personnel, from the contact center can attend to the patient.

The contact center may comprise a call center staffed with contact personnel or personal medical assistants, who can perform patient intake and facilitate the patient through the contact process. The contact center may comprise at least one server, computer, or device in communication with application server 105, such as to receive information from and transmit information to the application server and the patient device, in order to facilitate the intake and contact process. In at least one embodiment, the contact center may simply comprise a contact interface accessible via a contact device. Accordingly, the patient may be assigned an order of priority for a queue, or directly to a particular physician by the contact personnel based on the intake or interview, and/or based on the severity of the patient's condition or patient information, etc. In some embodiments the assignment of the patient may be at least partially automated based on the patient's information, request, and/or past history. In a preferred embodiment, the contact center and/or device feature is intended to provide a patient with 24-hour access to live personnel.

At least one physician may then be notified and/or connected to the patient, after pre-screening by the contact center. The physician may diagnose, treat, and/or prescribe for a patient via a communication channel established across the patient device, application server, and physician device, such as through video chat. The physician may offer treatments and/or prescribe medication, as well as insert script information and billing information accordingly. The physician may also access past patient information, such as through the application server or through a health records facility which may comprise at least a server and/or network housing electronic medical records of the patient.

A recording facility may log or record the communication between the physician and patient and may also log or record the communication between the contact personnel and patient. The recording facility may comprise at least one server in communication with application server 105 in order to record or retain a record of the communication between the patient and physician, or between the patient and the contact personnel.

In one further embodiment, the present invention is directed to a medical incident response and reporting system comprising a central server including a medical incident log module, and a patient profile module comprising a plurality of patient biographical and medical records. The system includes a contact center disposed in a communicative relation to the central server and includes at least one medical incident case manager communication device continuously monitored by at least one medical incident case manager. A patient communication device is provided which comprises an input component to facilitate transmission of information to a patient's biographical and medical record on the patient profile module of the central server, the patient communication device further communicative with the at least one medical incident case manager communication device via the central server to facilitate communication between the patient and the at least one medical incident case manager to evaluate the medical incident involving the patient. In at least one embodiment, the central server records all communications between the patient communication device and the at least one medical incident case manager communication device to the medical incident log module throughout a medical incident involving the patient. In at least embodiment, further includes the medical incident case manager communication device is operative to access the patient's biographical and medical records from the patient profile module.

The system, in accordance with at least one further embodiment, includes a medical incident response specialist communication device communicative with the central server and operative to dispatch a medical incident response specialist to the patient's location. A medical incident response station assembly is structured to be transported by the medical incident response specialist to the patient's location and comprises a medical incident response station location transponder communicative with the central server to continuously monitor the location of the medical incident response station assembly throughout the medical incident involving the patient. In one embodiment, the medical incident response station assembly further comprises a medical incident response station communication device also communicative with the central server to facilitate communication from the patient's location between at least the patient, the medical incident response specialist and the medical incident case manager, from the patient's location. Once again, in at least one embodiment, the central server records all communications between the medical incident response station communication device and the medical incident case manager communication device to the medical incident log module throughout the medical incident. The medical incident log module is configured to generate a final medical incident report of the medical incident involving the patient.

The present invention also comprises a method for medical incident response and reporting comprising at least the steps of: initiating a medical incident communication to a contact center by a patient via a patient communication device; assigning a medical incident case manager and connecting a medical incident case manager communication device to the patient communication device to facilitate communication between the medical incident case manager and the patient; conducting an initial medical incident severity assessment with the patient by the medical incident case manager; dispatching a medical incident response specialist to the patient's location; activating a medical incident response station assembly; initiating an on-site medical response; conducting an on-site diagnosis and implementing an on-site treatment regimen; conducting patient follow-up and confirming the patient completed the on-site treatment regimen; and generating a final medical incident report.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

For a fuller understanding of the nature of the present invention, reference should be had to the following detailed description taken in connection with the accompanying drawings in which:

FIG. 6 is a visual representation of a patient feedback form as part of the patient interface directed to at least one embodiment of a telemedicine system.

Like reference numerals refer to like parts throughout the several views of the drawings.

DETAILED DESCRIPTION OF THE PREFERRED EMBODIMENT

The invention now will be described more fully hereinafter with reference to the accompanying drawings in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As schematically represented, the present invention is generally directed to a system and method for telemedicine. The present system and method may relate to store-and-forward telemedicine, remote monitoring, and/or interactive telemedicine. For example, store-and-forward telemedicine may include first acquiring medical data such as imaging or bio-signals and assessment of the same by a medical professional. Remote monitoring may comprise managing chronic diseases or certain conditions including heart disease, diabetes, or asthma. Interactive telemedicine facilitates the real-time interaction between patient and provider and may include phone or online communication as well as home visits for emergency services and/or general health care delivery. Accordingly, the present system and method allows at least one physician to diagnose and/or treat at least one patient over a communications link or network.

Figure 1:
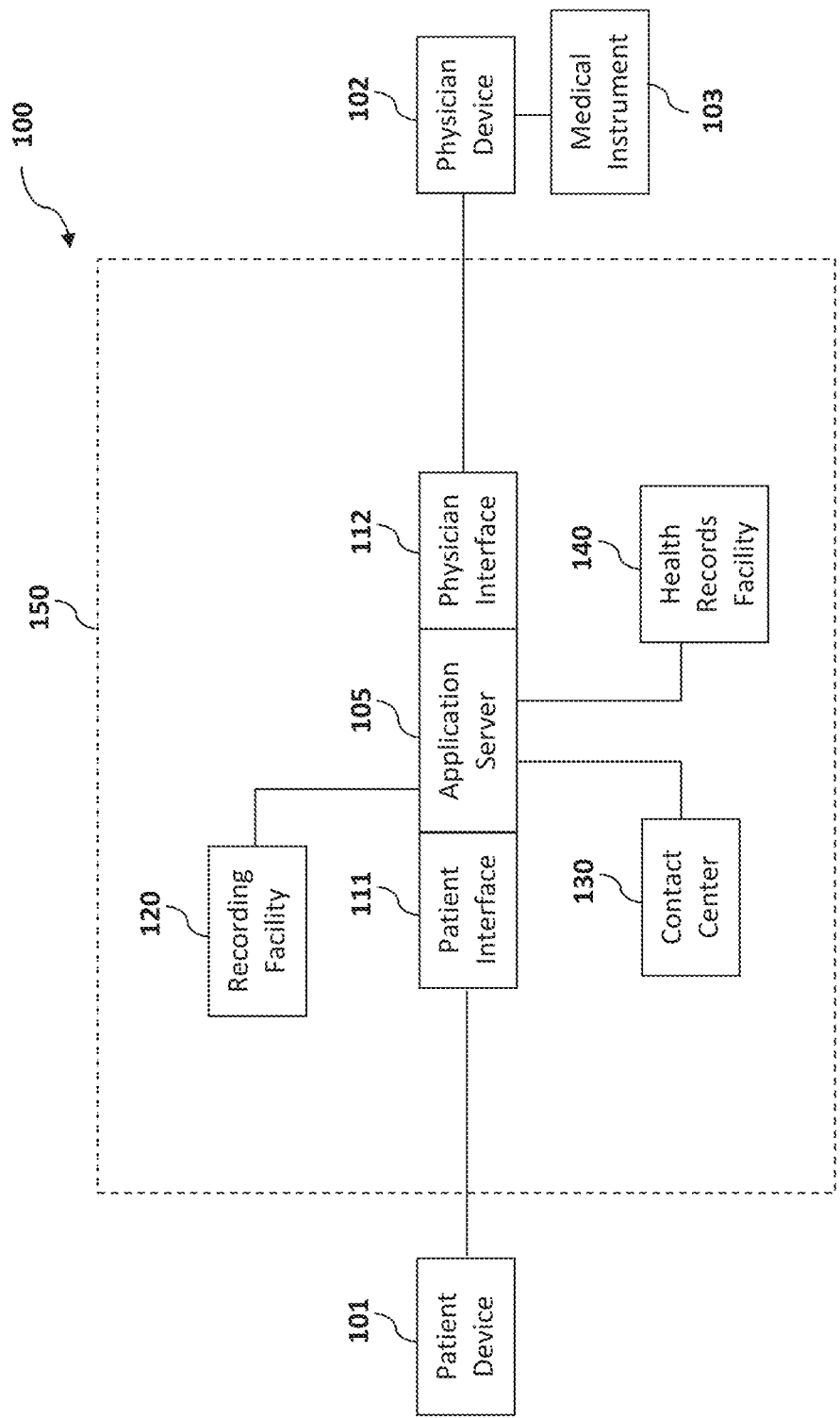
FIG. 1 is a schematic representation of one embodiment of a telemedicine system comprising a contact center.

In at least one embodiment, a system 100 for telemedicine may comprise a telemedicine application 150 accessible by a patient device 101 and a physician device 102, as generally represented by FIG. 1. Both patient device 101 and physician device 102 may comprise personal computer(s), laptop computer(s), tablet(s), mobile phone(s), wearable electronic device(s), Internet-enabled appliance(s), electronic kiosks, or any other processing device capable of accessing or executing telemedicine application 150. Accordingly, the patient device 101 may be collaboratively structured and/or configured to access the application server 105 through patient interface 111. Similarly, the physician device 102 may be collaboratively structured and/or configured to access application server 105 through physician interface 112. For example, the patient device 101 and/or the physician device 102 may access application server 105 through a proprietary software or mobile application and/or communications protocol on each of the devices, locally installed and executed on said devices. Alternatively, patient device and physician device may also the access application server 105 through a general Internet browser to access web-based interfaces, where telemedicine application 150 may be deployed as a software as a service (SaaS). In other words, the respective patient interface 111, physician interface 112 may comprise mobile applications, computer applications, and/or web browser applications installed on respective devices and having appropriate graphic user interfaces and programmed algorithms and network protocols that allow a user to perform the described functions set forth in this application.

Accordingly, the patient interface 111 and physician interface 112 may support operative communication with the application server 105 to corresponding patient device 101 and physician device 102, via any number or combination of Open Systems Interconnection (OSI) protocols. In certain embodiments, a contact interface 230 (FIG. 2) may further support operative communication between the application server 105 and the contact device 201 via similar protocol(s). For example, at least one embodiment of the present invention may utilize application layer protocols such as TCP/IP, web-based communication via HTTP, file transfer protocols such as FTP, TFTP, video or media streaming protocols such as RTP, SIP, and/or proprietary or operative-system or device specific protocols such as Apple Filing Protocol (AFP), Bell Labs Plan 9. It is understood that communications protocols may depend heavily upon the subjective design considerations of each application, and the present invention is understood to be capable of being implemented via various protocols or combinations thereof as known to those skilled in the art.

Telemedicine application 150 may comprise at least one computer accessible over a communications network and/or link, and computer software appropriately configured and programmed to allow for the functionalities described below. In at least one embodiment, telemedicine application 150 comprises an application server 105, a patient interface 111, a physician interface 112, a contact center 130, a recording facility 120, a health records facility 140, as well as the necessary communications link(s) for the transfer of information between or across the aforementioned components. Telemedicine application 150 may further comprise content delivery networks, cloud storage providers, or other computer(s), server(s) and any additional communications links and/or hardware to facilitate or improve the delivery speed and/or reliability of information.

Accordingly, application server 105 may comprise at least a general purpose computer, a special purpose computer, or an embedded system appropriate for facilitating or directing communications between at least a patient device 101 and a physician device 102. In some embodiments, contact devices 201 may facilitate the communication or prioritization of communications between patient devices and physician devices. As such, application server 105 may comprise appropriate hardware such as memory and at least a processor, operating system(s), software, databases, server applications, web-based applications, user interfaces or experiences (UI/UX) such as patient interface 111 and physician interface 112, as known to one skilled in the art. For example, the application server 105 may comprise LAMP, LYME, GLASS, LEAP, WISA, or any other solution stacks, web application frameworks, or other content management systems as known to those skilled in the art.

Figure 2:
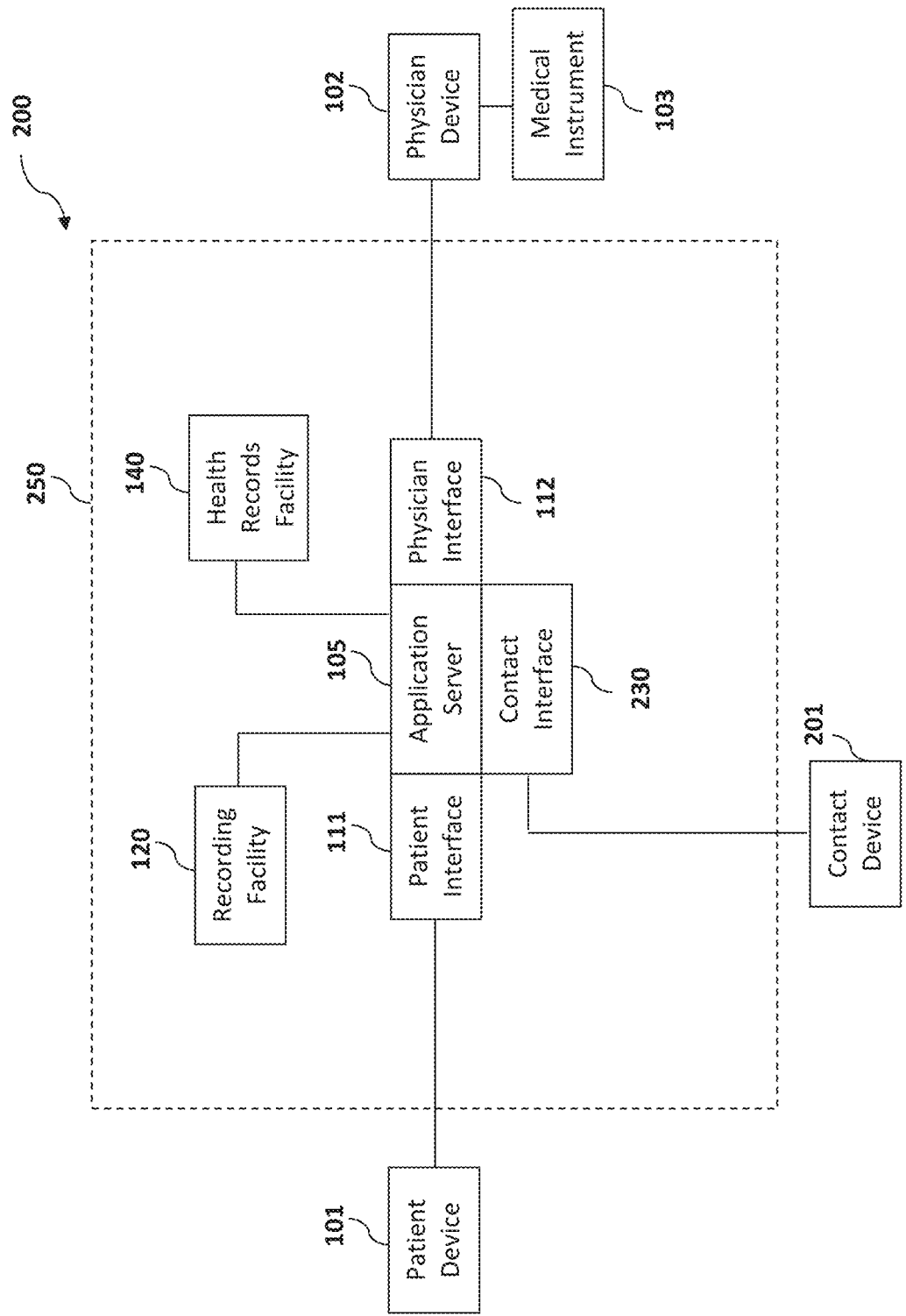
FIG. 2 is a schematic representation of another embodiment of a telemedicine system comprising a contact interface and contact device.

User interfaces may be used to transmit information to or receive information from the application server 105. User interfaces comprise a patient interface 111 accessible by a patient, a physician interface 112 accessible by a physician. In some embodiments, user interfaces may further comprise a contact interface 201 accessible by contact personnel, such as in application telemedicine application 250 as shown in FIG. 2. The user interfaces may be scalable and/or appear differently based on the device used to access the interface. The user interfaces may be stored locally as an application on the patient device 101, physician device 102, and/or contact device 201. Alternatively, the user interfaces may be stored or at least partially stored on the application server 105, such as in a cloud-based environment or application.

Figure 3:
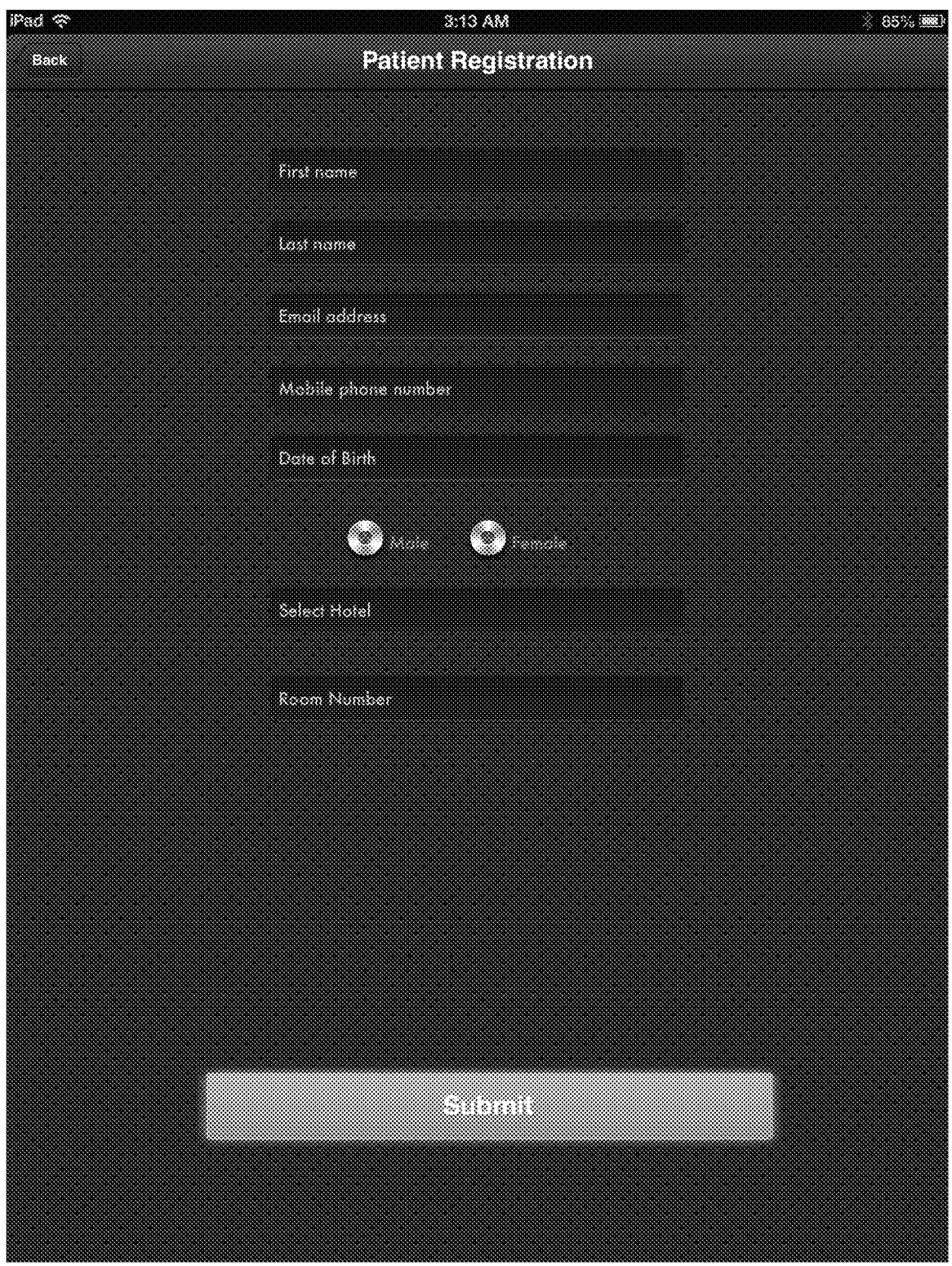
FIG. 3 is a visual representation of a patient registration form as part of the patient interface directed to at least one embodiment of a telemedicine system.

Accordingly, a patient may access a patient interface 111 in order to request medical assistance. The patient interface 111 may guide the patient through a registration process, such as illustrated in FIG. 3, if the patient is not yet registered with the application server 105. The registration process may ask the patient to input patient information such as his or her identifying information comprising name, government or state issued identification numbers such as driver's license, passport number, or social security number; contact information such as email address, telephone number, mailing address; demographic information such as age, sex, race; current location information such as hotel information and room number if the patient is traveling. The patient may be asked to agree to and/or sign various service agreements, disclaimers, waivers, or contracts in order to complete registration on the system including but not limited to patient consent forms, patient release forms, contracts for payment of fees and services, etc. Further, some embodiments might include an opt-out feature or other means for the patient to reject or refuse medical services. In some embodiments, such as in an emergency situation, a patient may not have to register or may be asked to register after medical assistance has been given. In yet other embodiments such as at a hotel or resort, the hotel may be able to subscribe to a group account and/or subscription and its patrons may be able to access the application server 105 through the hotel's account.

Figure 4:
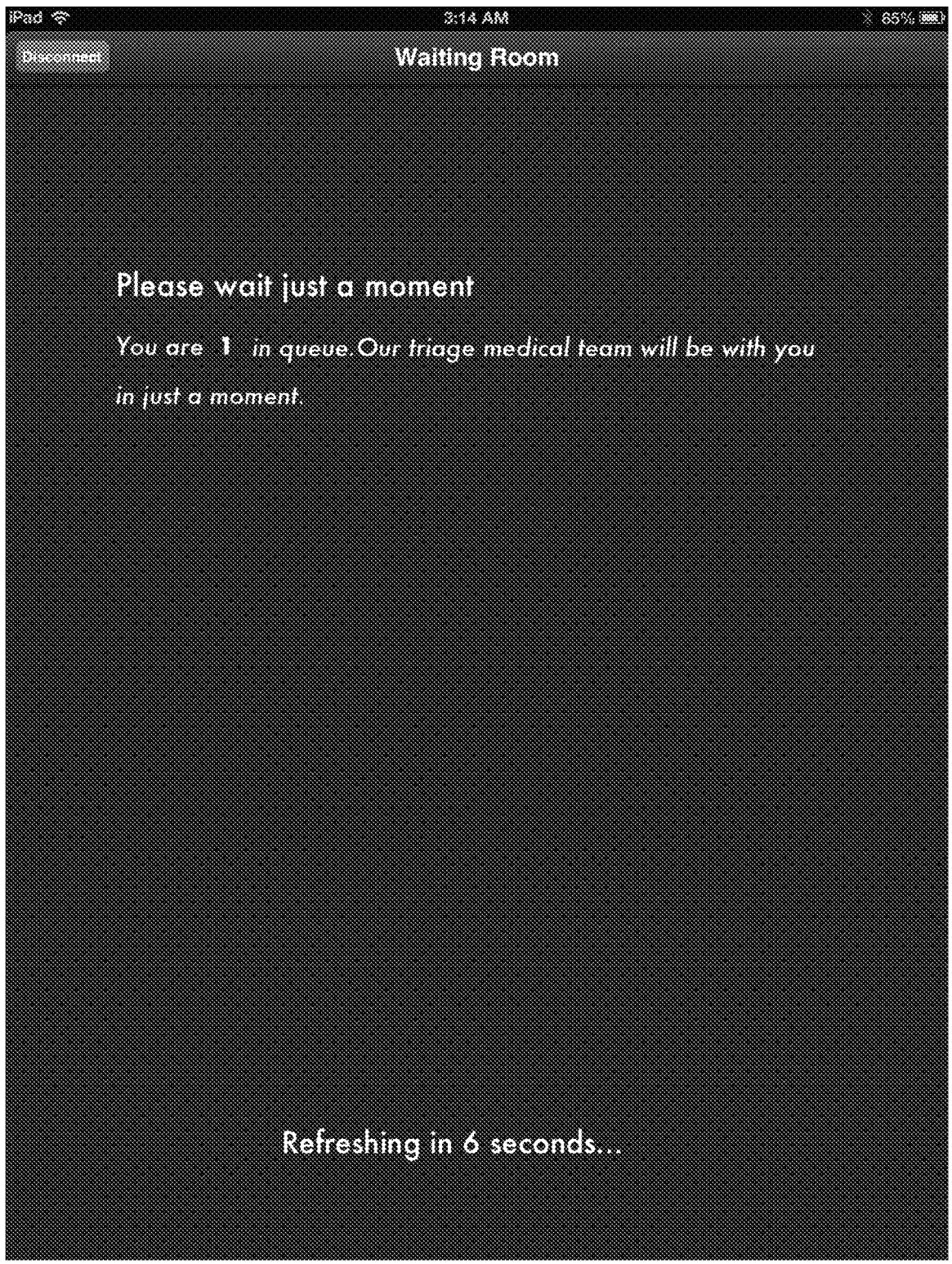
FIG. 4 is a visual representation of a patient queue as part of the patient interface directed to at least one embodiment of a telemedicine system.

If a patient is already registered or otherwise has access to an account, a patient may be prompted to login to his or her account, where the user may review the account history, change account information, make fee payments (e.g., by debit card, credit card, PAYPAL account, direct bank transfer, etc.), and renew prescriptions. After registration and/or login, a patient may request medical assistance from a physician or other medical professional. In at least one embodiment of the present invention, a patient, upon request for medical assistance through the patient interface 111, is first directed to a contact center 130 as illustrated in FIG. 1. The patient may be directed to a waiting room or queue, such as illustrated in FIG. 4, until contact personnel can attend to the patient. Following treatment, patients can be prompted to take surveys of various aspects of the telemedicine process.

Returning to the contact aspects of the present invention, the contact center 130 may comprise a call center staffed with contact personnel who can then facilitate the patient through a contact process. Contact personnel may comprise nurse practitioners or other trained professional appropriate for determining patient conditions. Accordingly, the contact center 130 may comprise at least one server, computer, or device in communication with the application server 105, such as to receive information from and transmit information to the patient device 101, either directly or through application server 105. Ideally, communication is transmitted through application server 105, such that recording facility 120 may record or document the ongoing communication between the patient device 101 and the contact center 130. In at least one embodiment, contact personnel may interview the patient via text, voice, or video chat, such as via a video module within the patient interface 111, illustrated in FIG. 5, to determine the priority of the patient's treatment based on the severity of their condition. A patient may be assigned a numerical priority, or a priority based on a predetermined contact scheme. For example, a patient may be prioritized by a contact personnel under conventional classifications comprising black (so severely injured that they will die of their injuries), red (require immediate intervention but are likely to survive), yellow (condition is stable but requires watching), green (require care but not immediately), white (minor injuries in which first aid and home care are sufficient). Of course, other systems such as various scoring systems (Contact Revised Trauma Score or TRTS, Injury Severity Score or ISS), the S.T.A.R.T. model, various hospital systems, as well as other systems known to those skilled in the art may also be used. In other embodiments, the contact center 130 may be partially or entirely automated, whereby patients may be directed depending on their input into the system. In some embodiments, a patient may only be directed to a contact center 130 in emergency situations.

Figure 8:
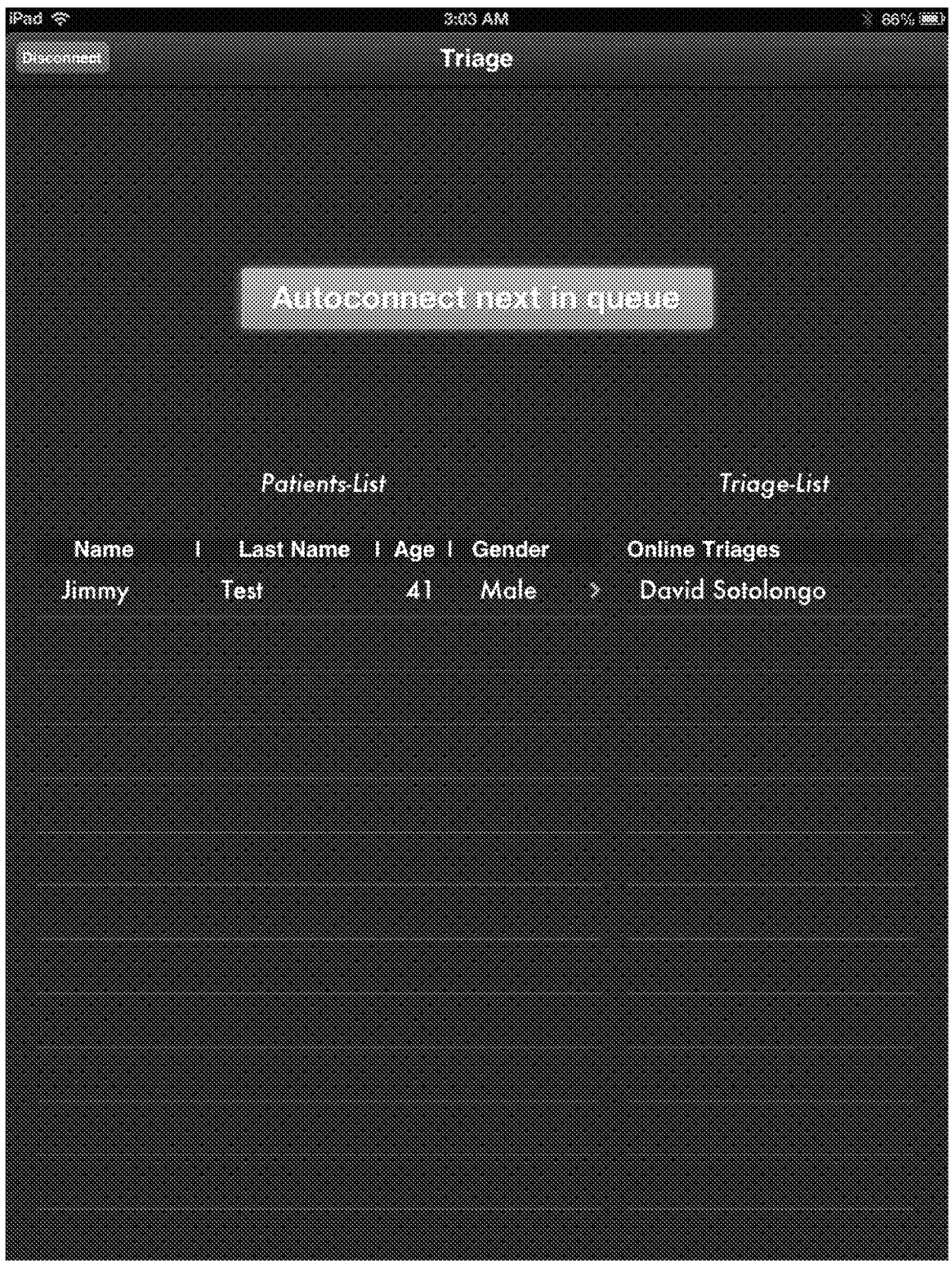
FIG. 8 is a visual representation of a contact list as part of the contact interface or contact center directed to at least one embodiment of a telemedicine system.

Further, in the embodiment of FIG. 2, contact personnel may perform contact through a contact device 201 remotely, rather than performing the function from the contact center 130. In other words, the contact center 130 may comprise at least a contact interface 230 and at least one contact device 201. Accordingly, contact personnel may be able to register and/or login to application server 105 in order to perform contacts on incoming patients. Contact personnel may also connect to patients awaiting contact either manually or automatically, such as illustrated in FIG. 8, which may present the contact personnel with patient information and current status. Contact personnel may be able to filter the patient list such that only those still awaiting contact will show. Patients may be listed in order of request, or alternatively in order of priority, e.g. a patient may have selected or inputted whether the matter was urgent or not urgent.

Figure 5:
FIG. 5 is a visual representation of a video chat as part of the one or more user interface(s) directed to at least one embodiment of a telemedicine system.

Accordingly, after a patient undergoes contact, the patient may then be placed in another queue, a position in a queue, or directed immediately to a medical professional, based on the severity of his or her condition as determined by the contact personnel. If the patient is placed into a queue, the patient may be presented with an approximate wait time and/or the current position in queue. After the queue, the patient will be connected to at least one physician or medical professional. The matching of patient to physician may be performed manually by the contact personnel, the physician, and/or automatically based on condition of the patient and/or the specialty of the physician. Accordingly, the patient will enter into a video chat with the selected, matched, or next available physician in at least one embodiment comprising audio and visual communication, such as a video chat room as illustrated in FIG. 5. The physician may then diagnose the patient and provide treatment and/or prescriptions. Of course, in other embodiments a patient may have direct access to a medical professional, such as the patient's primary care physician, or a physician who has treated the patient in the past.

Figure 6:
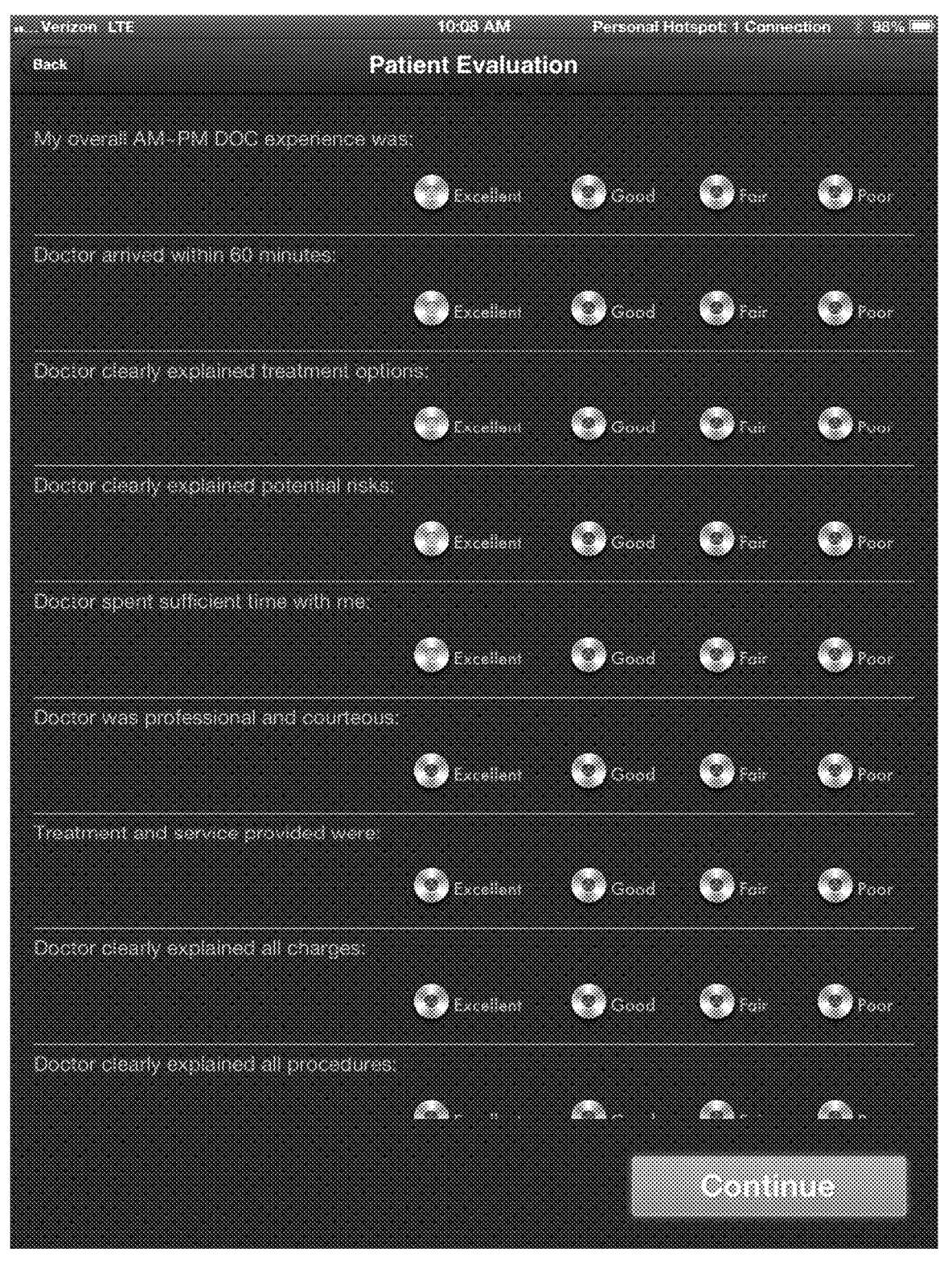
Figure 7:
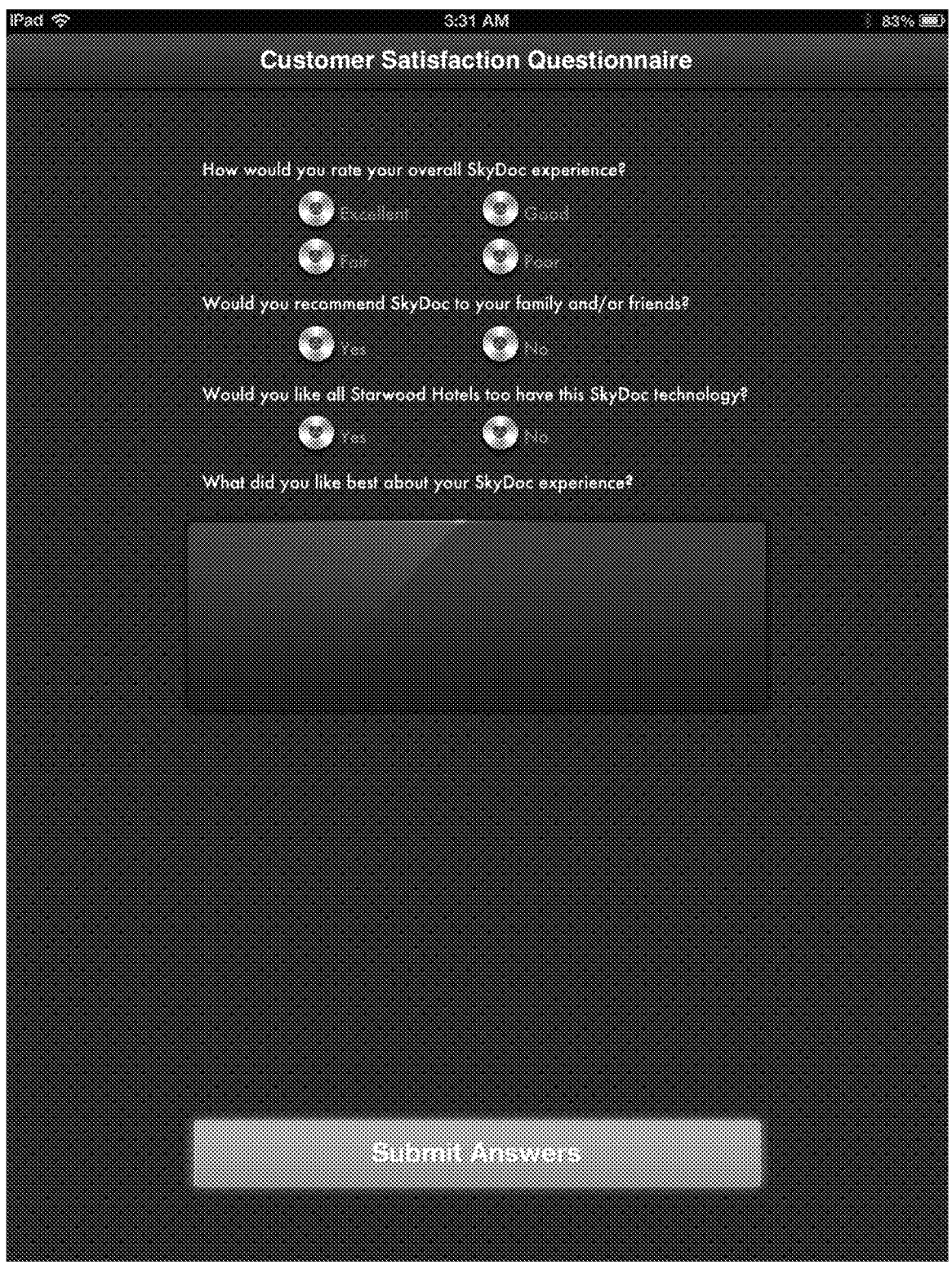
FIG. 7 is a visual representation of another patient feedback form as part of the patient interface directed to at least one embodiment of a telemedicine system.

A patient may also perform an evaluation and/or comments or feedback after diagnosis and/or treatment via an evaluation module in the patient interface 111, as illustrated in FIGS. 6 and 7. Patient evaluations may be conducted via a form format and/or may also be conducted by video, such as through recording and archiving a patient's audio and visual comments and feedback. Speech recognition software or algorithms may be employed to provide an automated transcript of a patient's audio feedback. In at least one embodiment of the present invention, patient evaluations may be automatically or partially automatically transmitted by the application server 105 to predetermined third parties, such as an evaluating physician or medical professional's employer, a common carrier or hotel where the patient is presently residing and seeking care, and/or to the treated patient's insurer, in order to ensure quality of care.

In a preferred embodiment of the present invention, the application server may automatically schedule continuity of care items for the patient upon conclusion of the patient evaluation. These continuity of care items may include notifications, follow-ups, patient reassurance messages, informational or educational material regarding the patient's condition or evaluation. Specifically, the continuity of care may comprise call backs via phone, email, text, and/or mobile application notifications at predetermined intervals, such as at 1 hour, 24 hours, and 48 hours after the treatment. In a push notification embodiment, a notification module may be programmed and configured on the patient interface 111 and software, such as to receive notifications from the application server 105 through input by the contact center 130. For example, a patient may receive a notification at 1 hour after the exam, requesting the patient to complete a follow-up evaluation, such as to respond as to the effectiveness of the treatment and/or whether additional treatment is requested. A scheduler may be integrated as a continuity of care item for scheduling a follow-up call with the physician and patient or with a second physician for another opinion, depending on the patient response or feedback.

The physician similarly accesses application server 105 via a physician interface 112 in order to diagnose and/or treat the patient. New physicians may be able to register via the physician interface 112 in order to create an account. In at least one embodiment, registrations may be invite-only, such that only preselected physicians may register and or use the system. In other embodiments, any physician or healthcare professional may be able to register. The registration process may ask the physician to input his or her identifying information such as name, government or state issued identification numbers such as driver's license, passport number, or social security number; contact information such as email address, telephone number, mailing address; educational and career information such as credentials, schools attended, graduation information, medical specialty or specialties; demographic information such as age, sex, race; licensing information such as medical board registration number. New physician registrations may be authenticated manually or automatically via informational databases and/or medical board databases. If the physician has registered and/or that registration has been validated, the physician may then login to his or her account via the physician interface 112.

Figure 10:
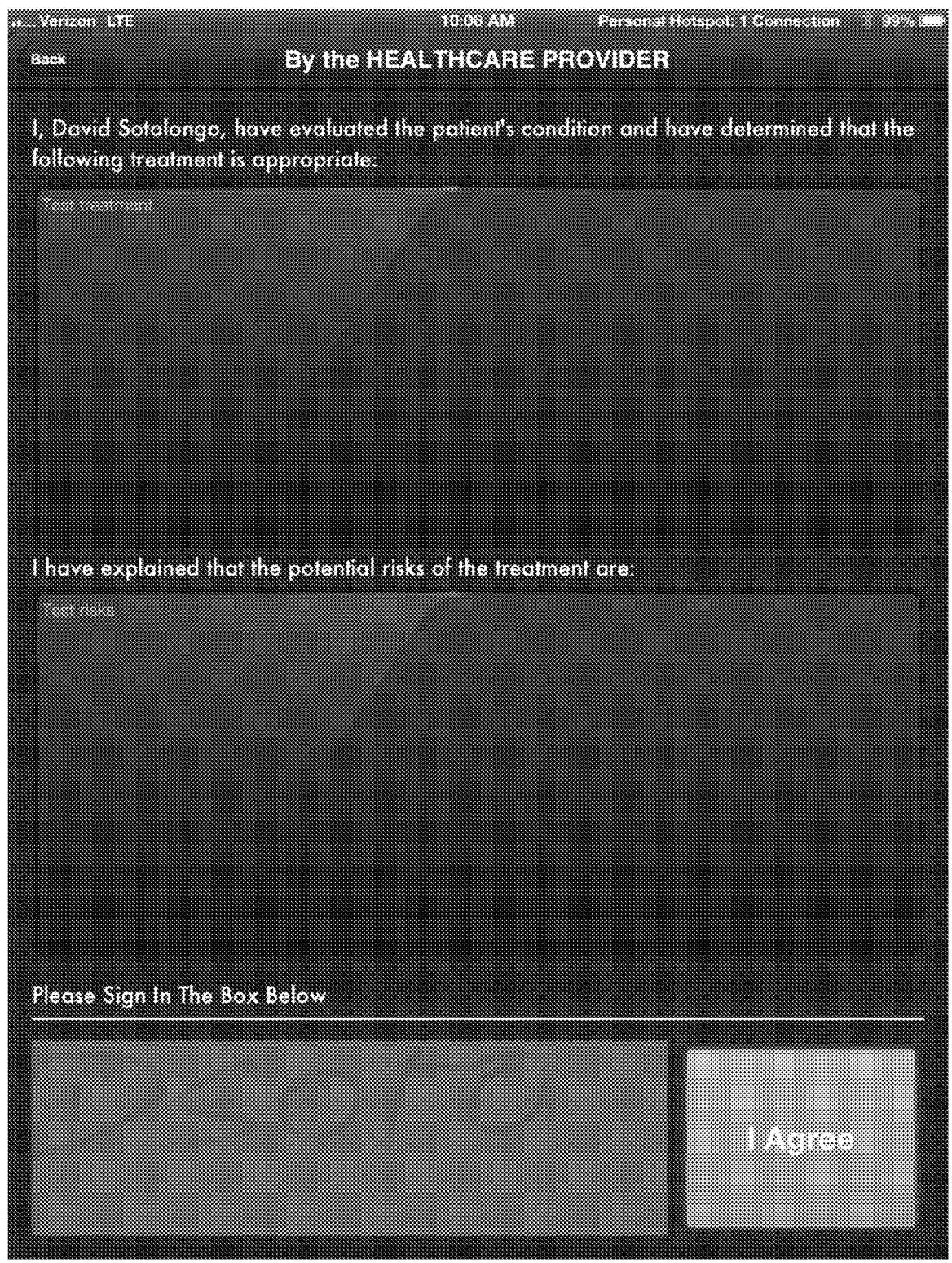
FIG. 10 is a visual representation of a diagnosis and treatment form as part of the physician interface directed to at least one embodiment of a telemedicine system.
Figure 11:
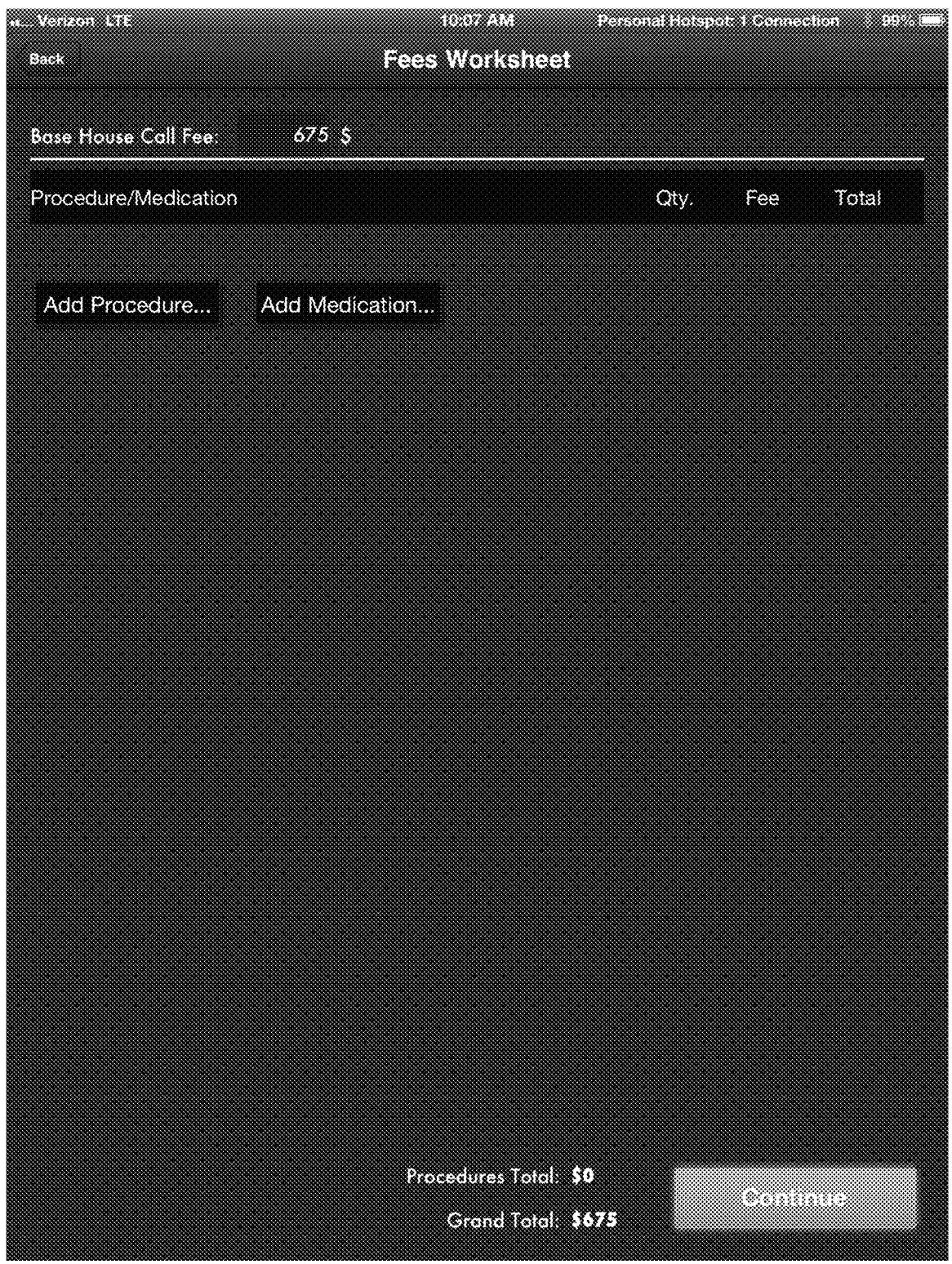
FIG. 11 is a visual representation of a fee worksheet as part of the physician interface directed to at least one embodiment of a telemedicine system.
Figure 12:
FIG. 12 is a visual representation of a fee worksheet as part of the physician interface directed to at least one embodiment of a telemedicine system.

The physician may have access to at least one patient selectable via physician interface 112, such as patient(s) currently awaiting treatment that were directed by the contact center 130 and/or a contact device 201. In at least one embodiment the physician may receive an alert via SMS, phone, email, or via the physician interface 112 which may run in the background of a computer or mobile device, notifying that a patient is awaiting treatment and/or has been directed to the physician. The physician may diagnose a patient in a video chat room, similar to FIG. 5 above. After the diagnosis, the physician may fill in treatments and/or prescriptions accordingly, as illustrated in FIG. 10. Fees may also be calculated manually or automatically, as shown in FIGS. 11 and 12. The cost of services may be predetermined by the application server 105 and/or may be modified by the physician. In some embodiments, application server 105 may be in communication with an insurance facility and/or government facility such as to directly transmit the procedures performed and fees incurred. Information to be transmitted related to the procedures may further comprise associated International Statistical Classification of Diseases (ICD) codes.

Figure 9:
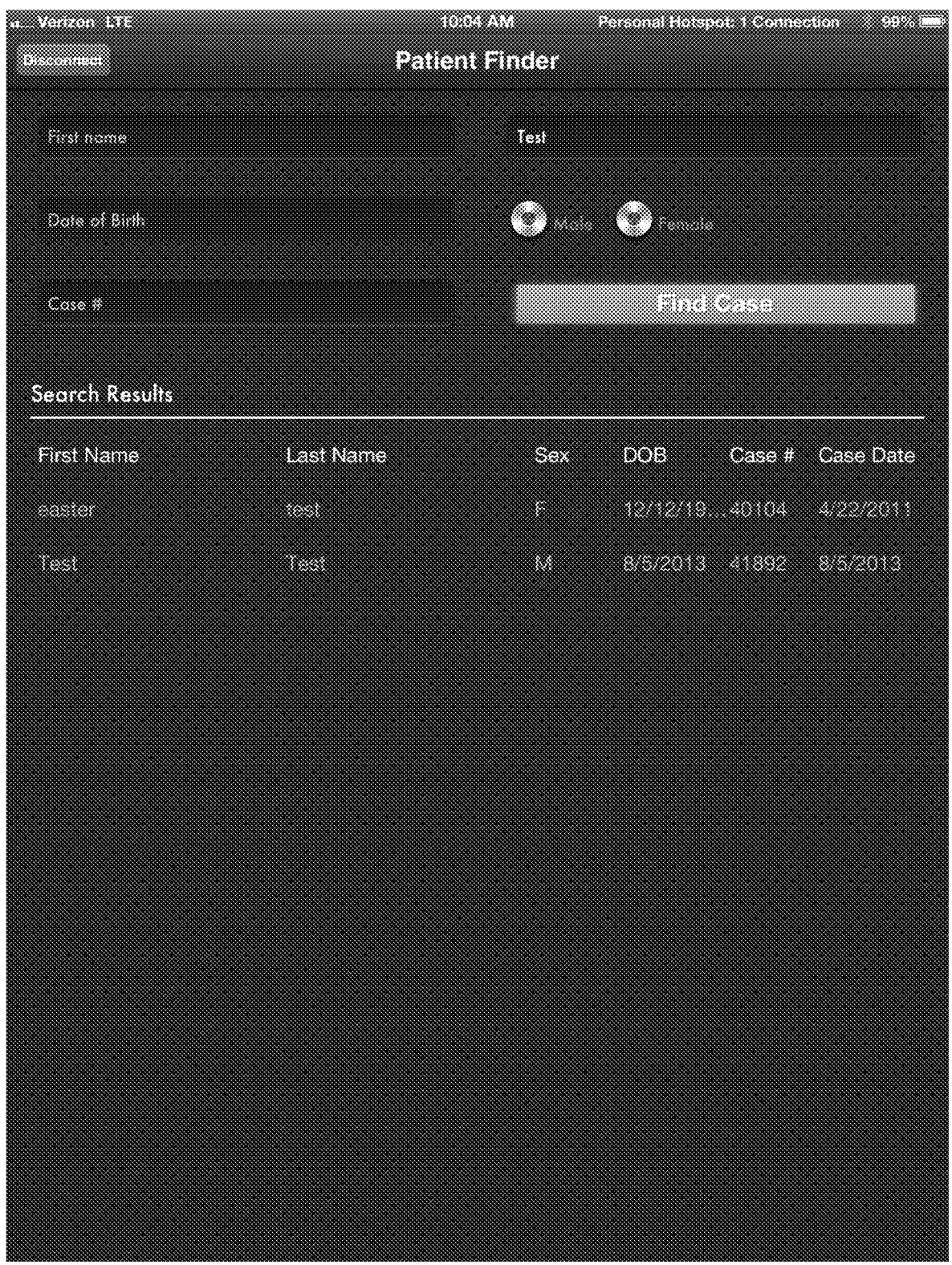
FIG. 9 is a visual representation of patient cases as part of the physician interface and/or the contact interface directed to at least one embodiment of a telemedicine system.

The physician may also access past patient information, such as previous patients directed to the physician and/or patients that the physician has diagnosed in the past. In at least one embodiment the physician may be able to search for a patient via name, date of birth, case number, or other patient information, as illustrated in FIG. 9. Accordingly, the application server 105 may comprise permission settings for each physician such that only certain patients may be viewable or searchable by a particular physician. In at least one embodiment, patient information may be stored on the application server 105, which may be searchable, retrievable, or otherwise accessible by the contact personnel and/or physician. In other embodiments, the health records facility 140 may store at least a portion of the patient information.

The physician may perform evaluations and/or comments or feedback after diagnosis and/or treatment of a patient via a reverse evaluation module, similar to the views illustrated in FIGS. 6 and 7 except through a physician interface having alternative parameters. This reverse evaluation of the client-patient by the service provider or physician is beneficial in several respects. Most importantly, it allows the physician to flag problematic patients and to keep an ongoing record outlining certain red flags from multiple physicians who may evaluate the patient. In one example, this reverse evaluation may help flag patients who might seek repeated treatments for various drug prescriptions. As another example, patients with a history of positive feedback may be selectively targeted for continuing business and/or promotions. Importantly, this record tracking will serve as an important tool in providing objective evidence for reducing possible liability as well as for deterring frivolous malpractice or other lawsuits by a patient.

As such, in at least one embodiment of the present invention for reverse evaluation, a physician may similarly rate a patient as "Excellent", "Good", "Fair", "Poor", or out of a predetermined numerical scale. A fill in the blank comments section may allow a physician to insert comments, concerns, or opinions. The reverse evaluations may similarly be conducted via a form format and/or may also be conducted by video, such as through recording and archiving a patient's audio and visual comments and feedback.

The health records facility 140 may comprise at least one server in communication and accessible by application server 105 which may be commonly managed along with the application server 105 and/or managed by a third party such as a hospital, government agency, or commercial provider. The health records facility 140 may comprise a network of servers and may integrate and/or verify various records and information from various sources, such as from the Center for Medicare & Medicaid Services (CMS), an electronic health record (EHR) network or clearinghouse, or individual health networks or hospitals. The health records facility 140 may adopt one of a plurality of HER specifications, such as but not limited to open EHR, Virtual Medical Record by HL7, SMART, as well as other specifications. The health records facility 140 may also be capable of cross referencing or synchronizing between various HER specifications in order to present a single complete, up-to-date patient history and/or record to the physician.

The recording facility 120 may log and/or record the communication between at least one physician and a patient. Recording facility 120 may also log and/or record communications between contact personnel and the patient. The recording facility 120 may also log and/or record the communication between a patient and local security personnel such as in connection with an incident report. Accordingly, the recording facility 120 may comprise at least one computer and/or server in communication with the application server 105 in order to record or otherwise retain a record of the communication between a patient and a physician, or a patient and contact personnel, or a patient and local security personnel such as in connection with an incident report. The recording facility 120 may comprise a secure cloud storage facility, but may also comprise at least one server at a location proximal to the patient, such as at a hotel, resort, or other premises that the patient is staying at. The recording facility 120 may also utilize existing commercial cloud storage options such as Apple iCloud, Amazon S3, Rackspace, or other like storage options. The recording facility 120 may be accessible by insurance personnel or an insurance company for claim purposes. The recording facility 120 has the intrinsic benefit of providing proof and documentation to deter unnecessary litigation, and may be helpful in the oversight and quality control of the contact personnel and physician. As such, the recording facility 120 may automatically record each communication through the application server 105 as a video and/or audio file. The video and/or audio file may be stored in any number of compression formats known to those skilled in the art, such as but not limited to AVI, DIVX, MP3, MP4, H264, MPEG, FLV. The recording facility 120 may also automatically associate each file with a directory and/or metadata comprising patient information, physician information, time of treatment, type of treatment. The recording facility 120 may further comprise a tamper-evident mechanism such as a cryptographic hash function or electronic signature, using hardware encrypted full disk drives, or other methods known to those skilled in the art to ensure validity and originality of the recorded file and associated data. The recording facility 120 may be compliant with the Health Insurance Portability and Accountability Act (HIPPA) in a preferred embodiment. In a preferred embodiment the entire process and all interactions by the patient and the present application or invention is recorded, from contact intake to the entirety of the medical exam.

The recordings may be searchable via a video archive interface by a number of search parameters, including patient name, date of treatment, physician name, contact personnel name, type of medical exam, type of drug prescription, by insurance carrier, as well as other appropriate parameters.

Figure 2A:
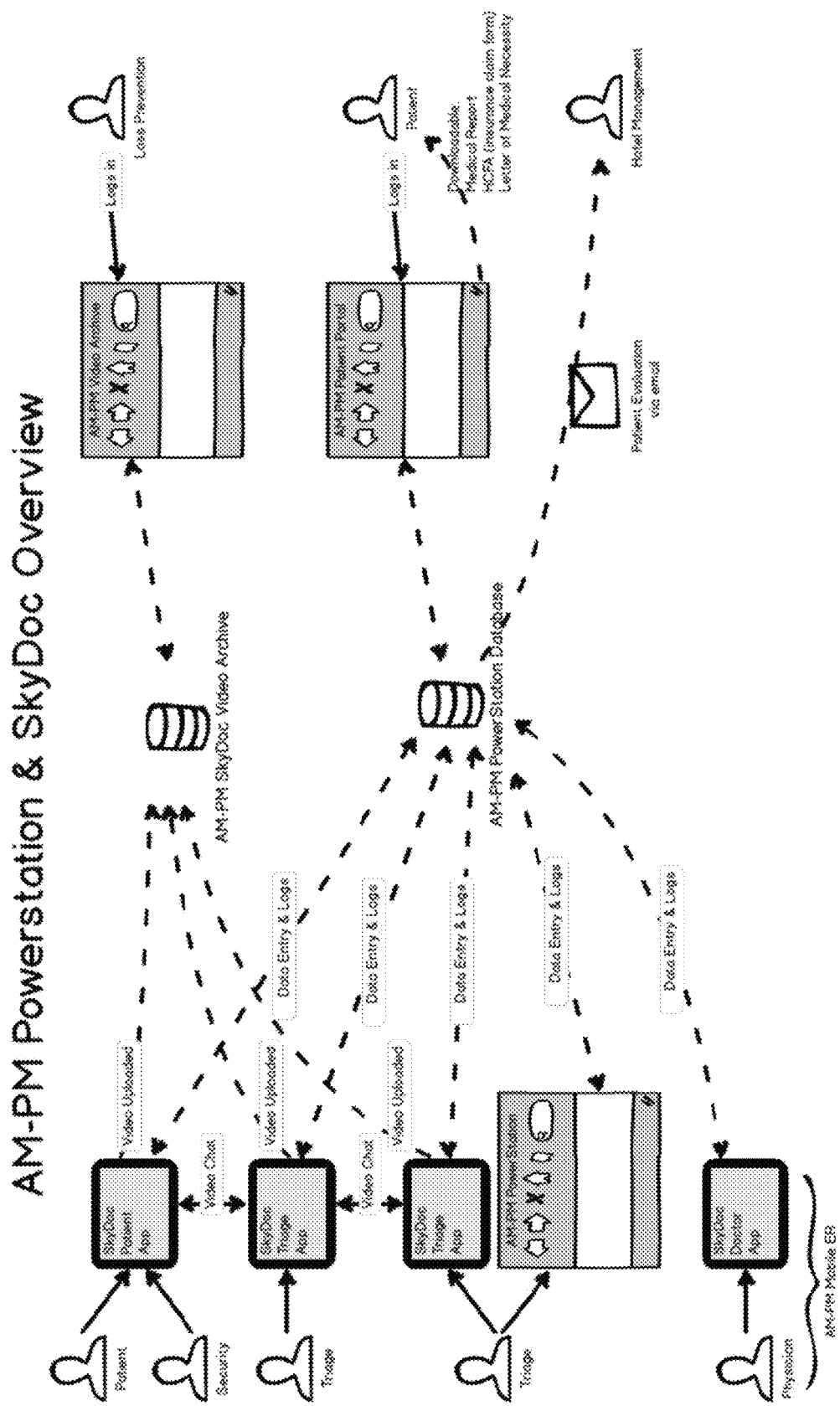
FIG. 2A is a schematic representation of another embodiment of a telemedicine system comprising a plurality of devices and interfaces.

With reference to FIG. 2A, the above-noted functionalities are depicted as an interactive plurality of operators, who collectively utilize the respective devices and interfaces to carry out a novel sequence of telemedicine-related activity. As depicted, the users of the system include patients, contact specialists, physicians, security personnel, loss prevention specialists, hotel/premises management personnel, etc. Accordingly, the inventive system and method facilitates a great deal of functionality, not only in diagnosing and treating patients, but also in storing and processing related date surrounding the patients and their particular circumstances at a given time and place. The inventive system further permits value added post processing techniques such as risk mitigation, loss prevention, medical records management, etc.

Figure 13:
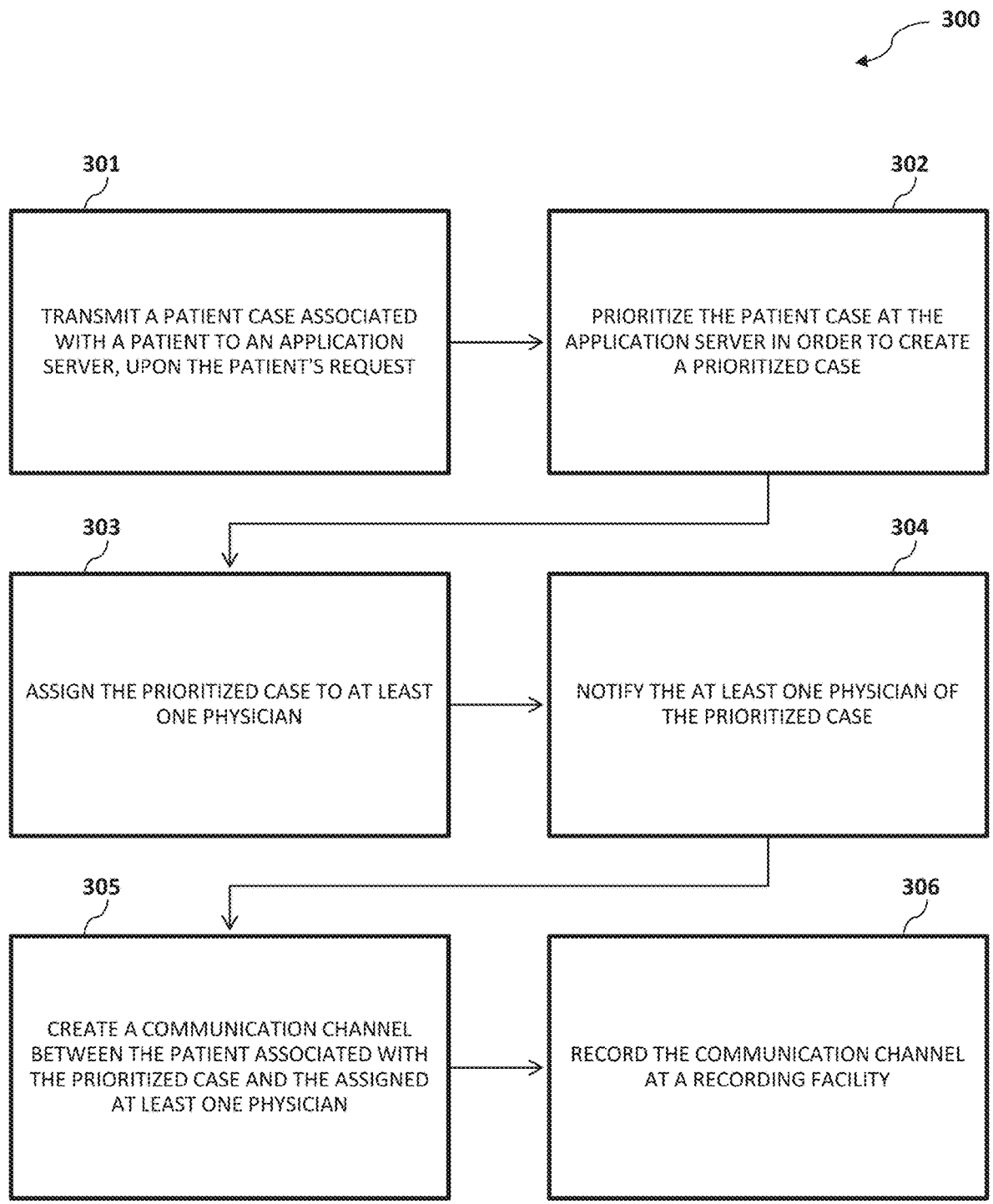
FIG. 13 is a schematic representation outlining the steps of one preferred embodiment of the present invention.

Still another embodiment of the present invention may comprise a method directed to telemedicine as generally illustrated by FIG. 13. Accordingly, a patient case associated with a patient is first transmitted to an application server, such as in 301. The patient case may comprise patient information as described above. In some embodiments, the application server may also authenticate, match, and/or add additional information from a health records facility which may make available, to a physician, the past medical history and other appropriate supplemental information related to a patient, and this may occur at any step in the process, or upon the request of a contact personnel or physician.

Each patient case transmitted to the application server is then prioritized, as in 302, in order to create a prioritized case. A prioritized case may comprise the original patient case, but with additional priority data that may facilitate in the assignment of a patient case with one or more particular physician(s). Priority data may be inputted by contact personnel as described above, such as the assignment of a numerical or categorical priority order based on the severity of the patient's condition, and may be based on a number of known contact schemes or a proprietary scheme. In a preferred embodiment, the priority data would be inputted by contact personnel after an initial video consultation or intake where the patient's condition can be assessed in real time.

Priority data may also be at least partially automated by a predetermined matching scheme, which may be based in part on information provided by the patient. For example, if the patient case indicates that the patient is suffering from a heart condition, the patient may be directed to a cardiologist. In another example, if the patient case indicates that the case relates to a recurring problem and/or a case that requires follow up, the priority data may indicate such and the patient may accordingly be prioritized to be connected to a previous physician that diagnosed the problem.

Accordingly, the prioritized case is assigned, as in 303, to at least one physician, either by contact personnel, by using a predetermined matching scheme, or a combination of the two. In some embodiments, a plurality of physicians may be assigned a prioritized case either concurrently or sequentially. The assignment step 303 may comprise linking of or otherwise allowing access to the prioritized case. As such, an assigned physician may be able to access the prioritized patient case or prioritized case through the application server through a physician device and/or physician interface as described above.

Upon assignment of a prioritized case, at least one physician may be notified, as in 304. Accordingly, a physician may receive an email, a SMS text, a phone call, a mobile alert through a mobile application on the physician device in communication with the application server, or other methods or communication protocols of notification to transmit a notification, message, or data packet from the application server to the physician device, as described in greater detail above.

Accordingly, in some embodiments, information or data from the patient case may be transmitted directly to the physician device along with or in place of notifying the physician. In a preferred embodiment, however, at least a portion of the information and data related to the patient and/or patient case are stored on the application server or at a health records facility accessible by the application server, in order to ensure privacy, safety, and integrity of the patient case data. Accordingly, in at least one embodiment, the physician device, software, and/or physician interface may not cache any data on the local physician device. Rather, information may only be accessible when the physician device is connected to and authenticated by at least the application server and/or health records facility. As such, access to the patient case or prioritized case may be made available to the physician proximate to step 304, preferably upon assigning the prioritized case to the at least one physician as in step 303.

As a next step, a communication channel between the patient associated with the prioritized case and the assigned at least one physician may be created, as in 305. The communication channel may be activated upon an assigned physician's request, such as through click of a button through physician interface, or otherwise responding to the notification sent to the physician device. The physician may have continued access to the patient record during the communication with the patient, in order to assess the patient's past medical history and/or prior notes made by the same or a different diagnosing physician. The communication channel may comprise a voice and/or video chat, during which the physician may diagnose the patient and offer treatment and/or prescribe medication.

In a preferred embodiment, the communication channel between the patient and at least one physician is recorded, as in 306, at a recording facility. The recording facility, as described above, may comprise a cloud storage facility, or may simply comprise at least one server at a location proximal to the patient such as at a hotel or resort, aboard a bus, train, ship, plane or other common carrier, at a work facility or other facilities where remote medical may be performed. The record facility may be accessible by insurance personnel for insurance claim purposes.

In at least one embodiment of the present invention, compatible medical instrument(s) 103 may be utilized to transmit captured data directly to the application server 105. These medical instruments 103 may include Bluetooth, near-field communication, or other wireless stethoscopes, heart monitors, glucose monitors, oximeters, dermascopes, body scales, as well as other medical instrument that may be capable of scanning relevant parameters of a patient. The recorded images, information, and/or data from these instruments 103 may then be transmitted to the application server for further processing, review by other users such as for a second opinion by a second physician, and/or retrieval by the patient user. For example, from a physician-user perspective, the physician may save, store, auto-fill, or otherwise populate an electronic medical record of a patient using data retrieved directly from the one or more medical instruments 103 described above. As another example, the physician may share data from the one or more medical instruments 103 with a second physician live during the existing video communication with the current client, via the physician interface.

The application server 105 may be configured to forward invoicing or health insurance claim forms directly to an insurance company, Medicare, Medicaid, or other predesignated third parties, based on patient's respective inputted insurer. Similarly, the application server 105 may forward a patient's prescription information directly to a predetermined pharmacist. The predetermined pharmacist may be at least partially automatically determined by the application server 105 such as by geographical address or location matching of a patient's present address with the closest pharmacists. In yet other embodiments, real time delivery services may be employed, whereby a GPS on a patient mobile device is employed for delivery of a prescription. Alternatively, a house call physician may be dispatched to the location of a patient. Specifically, a graphic interface having GPS coordinates of a patient and the delivery personnel or dispatched physician may be shown through the patient interface on the patient device, as well as through a delivery interface on the delivery personnel's mobile device (or physician interface on the physician's device). Distance and/or direction may be indicated by way of known and appropriate navigation software. This feature may be particularly advantageous while the patient is traveling.

The application server 105, application 250, and/or more specifically the patient interface 111 may support the record keeping and retrieval of patient electronic records by a patient via a medical record module, including but not limited to electronic magnetic resonance imaging (e-MRI), health insurance claim forms (HICFA) such as CMS 1500 form including ICD codes, letters of medical necessity (LMN), lab results, x-rays, sonograms, medical diagnosis and opinions from one or more healthcare providers or physicians. Both typed and voice dictated data may be utilized and stored.

Individual components or elements of the system and method may be used interchangeably. The order of the method or processes described above may be arranged in any combination in various embodiments. In some embodiments, various steps may be omitted.

Figure 14:
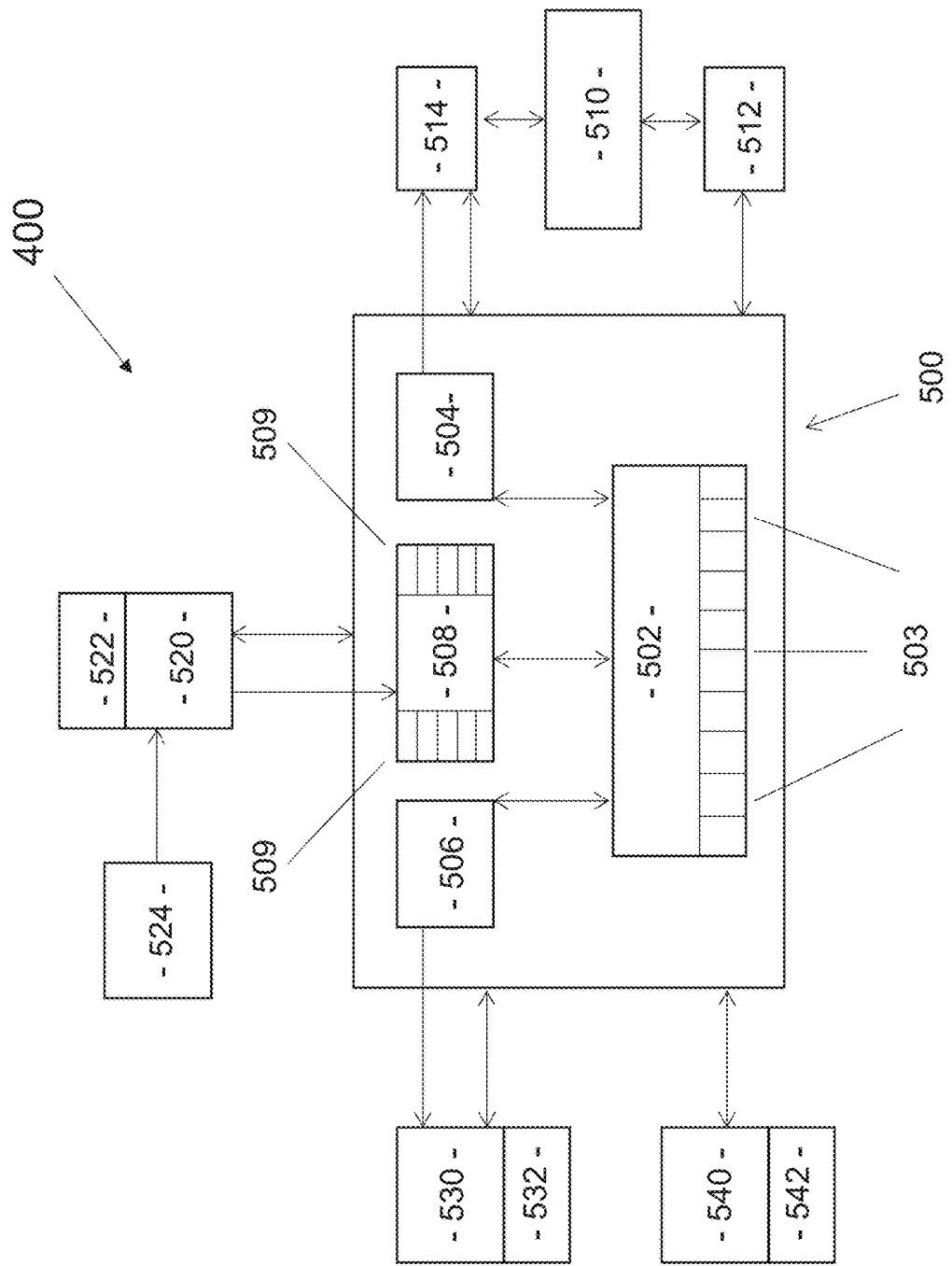
FIG. 14 is a schematic representation of one illustrative embodiment of a medical incident response and reporting system in accordance with the present invention.

Turning next to FIG. 14, a schematic representation of one illustrative embodiment of a medical incident response and reporting system 400 in accordance with the present invention is presented. A medical incident response and reporting system 400 comprises a central server 500. In at least one embodiment, a central server 500 is configured, among other things, to provide a communication network to facilitate communications between a plurality of communication devices of a medical incident response and reporting system 400, as described in greater detail hereinafter.

A central server 500 includes a medical incident log module 502, such as is shown in the illustrative embodiment of FIG. 14. A medical incident log module 502 creates and stores a unique medical incident log 503 for each and every medical incident which is handled via a medical incident response and reporting system 400 in accordance with the present invention. More in particular, each unique medical incident log 503 serves as a repository for, among other things, recordings between the various communication devices, once again, described in greater detail below, as well as various medical incident reports such as may be prepared by a medical incident case manager, a medical incident specialist, and/or medical incident response specialist, among others. Each unique medical incident log 503 is further utilized to store a final medical incident report, created via the medical incident log module 502 and corresponding to one particular medical incident handled via the medical incident response and reporting system 400 of the present invention. In at least one embodiment, a medical incident log module 502 is utilized to record, monitor and translate medical, security, private investigative and loss prevention data into live real time solutions. All video, audio and written, electronic and handwritten, data recorded are in encrypted and/or transcrypted formats in keeping with HIPAA and HRM standards.

In at least one embodiment, such as is shown in FIG. 14, a central server 500 further includes a patient profile module 508. A patient profile module 508 facilitates communication between a patient communication device 520 and the other communication devices described hereinafter which comprise a medical incident response and reporting system 400 in accordance with the present invention, via the central server 500. In at least one embodiment, a patient profile module 508 provides an initial point of contact between a patient communication device 520 and a central server 500.

In accordance with one embodiment, a patient communication device 520 is any device which allows at least audio, but preferably, audio and video communications, between a patient and a contact center 510, via a central server 500. As such, a patient communication device 520 in accordance with the present invention may comprise a landline telephone, a mobile phone, a smartphone, a tablet computer, a laptop computer, a desktop computer, etc. In at least one embodiment, a patient communication device 520 includes an input component which permits the transfer of alphanumeric data, files, photographs, audio and video recordings, etc., between the patient communication device 520 and the central server 500 in accordance with the present invention. As one example, an input component of a patient communication device 520 is utilized to create a patent's biographical and medical record which may include alphanumeric data, medical records, photographs, such as a photograph of the patient, audio or video records, etc.

In at least one embodiment, a patient communication device 520 comprises a patient communication device location transponder 522. As will be appreciated by those of skill in the art, almost every cell phone, smart phone, tablet computer, etc., available today is communicative with global positioning satellite ("GPS") systems, such that the location of the device can be continuously and precisely tracked, essentially anywhere on the planet. In some embodiments, a patient communication device location transponder 522 may continuously transmit and receive signals such that the location of the patient communication device 520 is known and tracked at all times. Alternatively, a patient communication device location transponder 522 must be activated prior to transmitting and receiving signals such that the location of the patient communication device 520 is known and trackable.

A patient communication device 520, in one embodiment, is a personal device under the care and control of the patient, such as may be owned or leased by the patient. In at least one alternate embodiment, a patient communication device 520 is a device under the care and control of a facility in which the patient is present. Such facilities may include, but are not limited to, hotels, resorts, spas, arenas, casinos, airports, yachts, docks, ports, etc., and the patient communication devices 520 are temporarily provided to a patient for use in the event of a medical incident involving the patient, so as to assure the patient obtains necessary medical treatment in response to the medical incident.

As will be appreciated from the foregoing, a patient's initial communication with a contact center 510 via a patient communication device 520 in accordance with the present invention may be a simple audio telephonic communication or text message initiated by the patient by dialing a nationwide, or worldwide, access telephone number. Alternatively, where a patient communication device 520 supports audio and video communications, the patient's initial communication with a contact center 510 via a central server 500 may be by way of a video teleconference. Further, where a patient's communication device 520 comprises a smartphone or computer, access to the contact center 510 via the central server 500 may be provided by way of a dedicated app which may be downloaded to a patient communication device 520, such as, once again, a smartphone, tablet, laptop or desktop computer, wherein the dedicated app facilitates audio and video communications, as well as the transfer of written communications and/or other alphanumeric data, medical records, photographs, audio or video recordings and/or remotely obtained patient diagnostic data, etc.

A patient profile module 508 is further utilized to create, store and update a unique biographical and medical record 509 for each and every patient involved in a medical incident which is handled via a medical incident response and reporting system 400 in accordance with the present invention. A patient's biographical and medical record 509 may be created and/or updated directly by a patient via an input component on a patient communication device 520. Alternatively, a patient's biographical and medical record 509 may be created by a medical incident case manager based upon information provided to the case manager by a patient. In at least one further embodiment, a patient's biographical and medical record 509 is updated by the central server 500 to include a final medical incident report corresponding to a medical incident involving the patient.

With reference once again to the illustrative embodiment of FIG. 14, a medical incident response and reporting system 400 in accordance with the present invention comprises a contact center 510, as referenced above. More in particular, a contact center 510 is disposed in a communicative relation with a central server 500 via a plurality of case manager communication devices 512, wherein each of the medical incident case manager communication devices 512 is continuously monitored by at least one of a plurality of medical incident case managers. As with a patient communication device 520, a medical incident case manager communication device 512 is any device which allows at least audio, but preferably, audio and video communications with a patient communication device 520. As before, a medical incident case manager communication device 512 in accordance with the present invention may comprise a landline telephone, a mobile phone, a smartphone, a tablet computer, a laptop computer, a desktop computer, etc.

A contact center 510 of the present medical incident response and reporting system 400 is staffed with at least a plurality of medical incident case managers twenty-four hours a day, seven days a week, fifty-two weeks a year. In accordance with at least one embodiment of the present medical incident response and reporting system 400, a contact center 510 at any given time will be staffed with no less than twenty-five medical incident case managers, twenty-five medical incident specialists, twenty-five security specialists, and twenty-five private investigative specialists and twenty-five personal protection specialists.

Once a patient involved in a medical incident initiates communication with a contact center 510 via a patient communication device 520, a medical incident case manager is assigned to the medical incident involving the patient. Once a medical incident case manager is assigned to the patient involved in the medical incident, the central server 500 establishes a communicative connection between the patient communication device 520 and a corresponding one of the plurality of medical incident manager communication devices 512, such that the medical incident case manager can establish and maintain communication with the patient. In accordance with at least one embodiment of the present medical incident response and reporting system 400, the medical incident case manager maintains communication with the patient throughout the entire medical incident involving the patient via the communicative connection between the medical incident case manager communication device 512 and the patient communication device 520. In accordance with at least one embodiment of the present invention, the central server 500 records all communication between a patient communication device 520, the contact center 510, and a corresponding one of the plurality of medical incident manager communication devices 512 to the unique medical incident log 503.

Once the medical incident case manager establishes communication with the patient, he or she will conduct an initial medical incident severity assessment with patient. More in particular, the medical incident case manager must first determine whether or not the patient requires emergency medical attention. In the event this is determined to be the case, the central server 500 identifies and contacts appropriate emergency medical responder(s) proximate the patient's location, as determined from the patient communication device location transponder 522. Further, in the event emergency medical responders are contacted and dispatched to the patient's location, the medical incident case manager will maintain communication with the patient, at least until such time as the emergency medical responders arrive at the patient's location, and the central server 500 records all communications between the patient communication device 520 and the medical incident case manager communication device 512 to the medical incident log 503. Similarly, the location of the patient communication device 520 as determined by the patient communication device location transponder 522 is continuously monitored by the central server 500, and the central server 500 continuously communicates the location of the patient communication device 520 to the emergency medical responders until such time as they arrive at the patient's location. Further, the central server 500 continuously records the location of the patient communication device 520, once again, as determined by the patient communication device location transponder 522, to the medical incident log 503 corresponding to the medical incident involving the patient throughout the medical incident involving the patient.

At the opposite end of the spectrum, during the initial medical incident severity assessment with patient, the medical incident case manager may determine that the patient requires no outside medical attention, and may instruct the patient regarding a self-treatment regimen which the patient may perform on themselves, where appropriate. Regardless, and as before, the central server 500 records all communications between the patient communication device 520 and the medical incident case manager communication device 512 to the medical incident log 503. Likewise, the central server 500 continuously monitors the location of the patient communication device 520 as determined by the patient communication device location transponder 522 and continuously records the location of the patient communication device 520 to the medical incident log 503 throughout the medical incident involving the patient.

In the event the medical incident case manager determines that the patient requires non-emergency medical attention, the central server 500 connects the patient with one or more medical incident specialist via a medical incident contact module 504. More in particular, the medical incident specialist contact module 504 allows a medical incident case manager to request a particular medical incident specialist including, but not limited to, a general practitioner, a cardiologist, a gastroenterologist, an internal medicine specialist, a neurologist, an obstetrician, a gynecologist, a pediatrician, a podiatrist, a urologist, etc., just to name a few. The central server 500 determines the availability of the requested medical incident specialist and contacts the appropriate medical incident specialist via the medical incident specialist contact module 504.

In accordance with at least one embodiment, the medical incident specialist contact module 504 of the central server 500 establishes a communicative connection between a medical incident specialist communication device 514 and the patient communication device 520. Thus, the medical incident specialist is able to proceed further with the remote diagnosis of the patient, and to better determine if a medical incident response specialist should be dispatched to the patient's location to implement an on-site treatment regimen.

In at least one further embodiment, the present medical incident response and reporting system 400 further comprises a portable diagnostic device 524. A portable diagnostic device 524 is structured to be operable by a lay person, such as the patient, and is able to measure one or more physiological parameters to facilitate a diagnosis of the patient's condition by a medical incident specialist or a medical incident case manager. In at least one embodiment, a portable diagnostic device 524 is about the size of a pen that may be carried in the patient's pocket or purse. In one further embodiment, a portable diagnostic device 524 is manufactured of a durable lightweight material, such as titanium. A portable diagnostic device 524 in accordance with the present invention may be physically interconnected to the patient communication device 520, such as via a data transmission cable, or it may be remotely communicative with the patient communication device 520 such as via bluetooth or other such wireless communication standard.

The physiological parameters measured by a portable diagnostic device 524 in accordance with the present invention include, but again are not limited to, one or more of temperature, heart rate, blood pressure, glucose level, uranalysis, etc. In at least one further embodiment, a portable diagnostic device 524 is operable to conduct an electrocardiogram. In yet another embodiment, a portable diagnostic device 524 comprises an otoscope. In addition to its diagnostic tools, a portable diagnostic device 524 in accordance with at least one embodiment of the present invention may include one or more additional features, such as, a high power flashlight, a regular camera for still or video recording, a dermatological camera, a security camera, an audio recorder, a safety security device, a safety security alarm, a medication holder, a laser pointer, etc. In at least one further embodiment, a portable diagnostic device 524 includes a location transponder, such as disclosed above with reference to a patient communication device 520. Still further, a portable diagnostic device 524 may be configured for quick remote access to a call center 510 of the present medical incident response and reporting system 400 via the central server 500 and/or to alert emergency responders via the 911 emergency response system thorough the central server 500.

In the event that the medical incident case manager and/or the medical incident specialist determine that an on-site medical treatment regimen is to be implemented, or that further on-site diagnosis is required, the central server 500 includes a medical incident response specialist dispatch module 506. Similar to the medical incident specialist contact module 504, the central server 500 utilizes the medical incident response specialist dispatch module 506 to determine the availability of medical incident response specialists proximate the patient's location, via a medical incident response specialist communication device 530 having a medical incident response specialist location transponder 532. The present medical incident response and reporting system 400 employs a plurality of medical incident response specialists strategically deployed throughout a coverage area for the system 400. Further, a sufficient number of medical incident response specialists are employed by the present medical incident response and reporting system 400 to assure continuous availability throughout the coverage area for the system 400 twenty-four hours a day, seven days a week, fifty-two weeks a year, with house calls in preferable 60 minutes or less.

A medical incident response specialist in accordance with one embodiment of the present invention may be a doctor, a nurse, a nurse practitioner, a paramedic, etc. In at least one embodiment, each medical incident response specialist is hand selected, credit checked, background checked, fingerprinted, bonded specially trained physician, physician assistant, nurse or nurse practitioner who specializes in house call medicine, medical hospitality, and hospitality medicine uniquely educated with evidence based protocols, procedures, policies, standards, systems and technologies. In yet one other embodiment, all medical incident response specialists are further uniquely trained and certified in security, private investigations, personal protection, and loss prevention solutions.

Once the central server 500 identifies an appropriate medical incident response specialist proximate the patient's location via a medical incident response specialist communication device 530, the central server 500 transmits a dispatch signal to the medical incident response specialist device 530, along with the patient's location and biological and medical record 509. The central server 500 further continuously communicates the location of the patient communication device 520, once again, by way of the patient communication device location transponder 522, to the medical incident response specialist communication device 530, until such time as the medical incident response specialist arrives at the patient's location.

In at least one embodiment of the present invention, a plurality of medical incident response specialists are employed by the present system 400 to provide, among other services: mobile electrocardiogram services monitored and clinically read by a board certified cardiologist at the call center 510; mobile sonogram services monitored and read by a board certified radiologist at call center 510; mobile x-ray services monitored and read by a board certified radiologist at the call center 510; mobile phlebotomist services with mobile blood diagnostics monitored and clinically read by a board certified emergency medicine or internal medicine specialist at the call center 510; mobile intravenous infusion services with multiple medical, pre- and post-surgical and nutritional variations provided by duly certified physician assistants or nurses monitored and clinically supervised by a board certified specialist at the call center 510; mobile anti-aging diagnostic and therapeutic modalities monitored and clinically supervised by board certified specialist at the call center 510; mobile stem cell therapeutic modalities to include harvesting, physical administration and stem cell infusions monitored and supervised by board certified specialist at the call center 510.

In at least one embodiment, the present medical response and reporting system 400 may be further employed to provide pharmaceutical delivery systems, including live and mobile, mailed, personal courier or via drone, delivered directly to the location of the patient or to a location specified by the patient on demand, twenty-four hours a day, seven days a week, fifty-two weeks a year. In at least one further embodiment, the present system 400 may be employed to provide mobile diagnostics like mobile electrocardiograms, mobile sonograms, mobile x-rays, mobile blood work, mobile IV infusions, mobile stem cell therapies, mobile anti-aging treatments, and monthly medical hormonal therapeutic deliveries.

Figure 15:
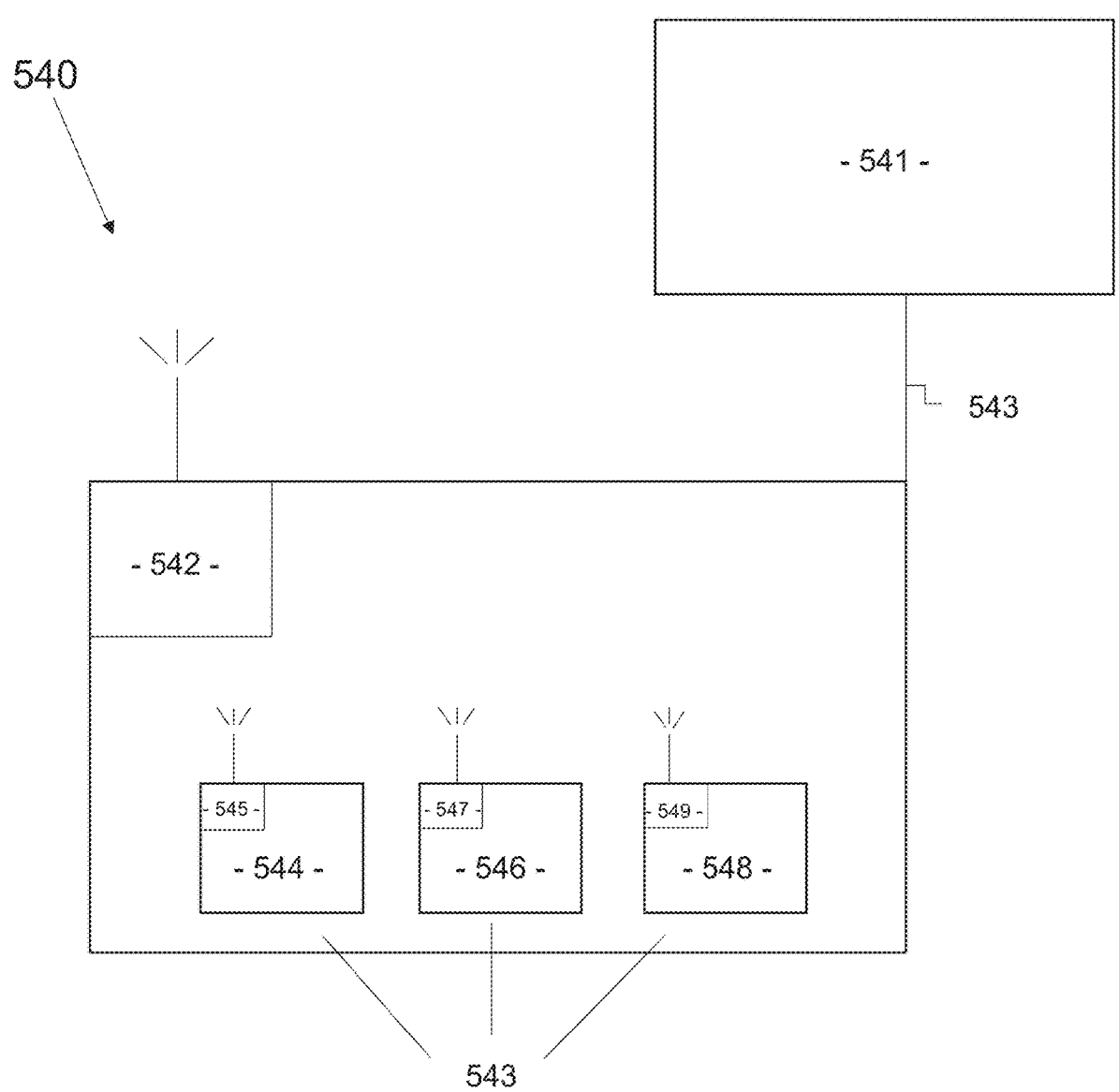
FIG. 15 is a schematic representation of one illustrative embodiment of a medical incident response station assembly in accordance with the present invention.

The present system medical incident response and reporting system 400 further comprises a medical incident response station assembly 540, such as is shown by way of example in the illustrative embodiment of FIG. 15. More in particular, a medical incident response station assembly 540 in accordance with the present invention is structured to be transported by a medical incident response specialist to the patient's location upon dispatch thereto via the central server 500 and the medical incident response specialist dispatch module 506. A medical incident response station assembly 540 in accordance with at least one embodiment of the present invention is constructed of material so as to be waterproof, fireproof, bullet proof, and temperature resistant.

In accordance with at least one embodiment, a medical incident response station assembly 540 is equipped with a plurality of preselected medical implements 543. The medical implements may include, but are not limited to, medical instruments 544, medical supplies 546, and medication 548. In at least one embodiment, each medical implement 543 is fitted with a radio frequency identification tag ("RFID"), for example, a medical instrument RFID 545, a medical supply RFID 547, or a medication RFID 549. More in particular, each RFID 545, 547, 549 is detectable, whether directly or indirectly, by the central server 500. As one example, each RFID may be detected by the medical incident response specialist communication device 530 and transmitted to the central server 500 therefrom.

More importantly, utilizing the plurality of preselected medical implements 543 comprising radio frequency identification tags 545, 547, 549, the central server 500 conducts a remote initial inventory of a medical incident response station assembly 540 to assure that all of the necessary medical implements 543 are present therein before a medical incident response specialist is dispatched to the patient's location with the medical incident response station assembly 540. In at least one embodiment, the central server 500 records the results of the remote initial inventory of the medical incident response station assembly 540 to the medical incident log 503 for the medical incident involving the patient. In one further embodiment, the central server 500 conducts a remote final inventory of the medical incident response station assembly 540 upon completion of an on-site medical incident response to determine which of the medical implements 543 were utilized and/or expended during the medical incident response.

In at least one embodiment, the central server 500 compares a present remote initial inventory of a particular medical incident response station assembly 540 with an immediately preceding remote final inventory in order to further verify, for example, that medical instruments previously utilized were properly sterilized, and/or that medical supplies 546 and/or medication 548 previously expended have been replaced.

With reference to the illustrative embodiment of FIG. 15, a medical incident response station assembly 540 comprises a medical incident response station location transponder 542 which is communicative with the central server 500. In at least one embodiment, the central server 500 continuously monitor the location of the medical incident response station assembly 540 once a medical incident response specialist has been dispatched to the patient's location. In one further embodiment, the central server 500 continuously records the location of the medical incident response station assembly 540 to the medical incident log 503 via the medical incident log module 502 throughout the medical incident involving the patient.

Once the central server 500 has dispatched a medical incident response specialist to a patient's location, the central server 500 will forward the biographic record of the medical incident specialist, including a summary of his or her medical and specialty training and a recent photograph, to the patient communication device 520 via the medical incident response specialist dispatch module 506. Further, the central server 500 will continuously update the patient, via the patient communication device 520, as to the exact location and estimated time of arrival of the medical incident response specialist as determined from the medical incident response specialist communication device location transponder 522 and/or the medical incident response station location transponder 542.

In at least one embodiment, a medical incident response station assembly 540 further comprising a medical incident response station communication device 541 which is communicative with the central server 500 to facilitate communication between at least the patient, the medical incident response specialist and/or the medical incident case manager, from the patient's location. As before, a medical incident response station communication device 541 may comprise a landline telephone, a mobile phone, a smartphone, a tablet computer, a laptop computer, a desktop computer, etc. In at least one embodiment, a medical incident response station communication device 541 comprises a video screen such that a medical response specialist may view the patient and the medical incident response specialist at the patient's location. In at least one further embodiment, a medical incident response station communication device 541 further comprise a video recorder such that the entire encounter between the patient and the medical incident response specialist from his or her time of arrival at the patient's location until his or her time of departure from the patient's location is recorded directly to the medical incident log 503 via the central server 500. More in particular, the central server 500 continuously records all communications between the medical incident response station communication device 541, the medical incident case manager communication device 512, and the medical incident specialist communication device 514 to the medical incident log 503 via the medical incident log module 502 throughout the medical incident involving the patient.

In at least one further embodiment, present system medical incident response and reporting system 400 comprises a medical incident response specialist recording device 534 which is worn on the person of the medical incident response specialist and is activated to begin recording audio and video from the moment the medical incident response specialist arrives proximate the patient's location until the time the medical specialist departs the patient's location. In at least one embodiment, a medical incident response specialist recording device 534 comprises a body cam. In at least one further embodiment, a medical incident response specialist recording device 534 comprises a body cam is attached to a custom made protective scrub which is donned by the medical incident response specialist before arriving at the patient's location and is worn by the medical incident response specialist the entire time until departure from the patient's location. In at least one further embodiment, a custom made protective scrub comprises bullet proof shielding therein.

The medical incident response specialist recording device 534 is communicative with at least the medical incident response specialist communication device 530, and the central server 500 activates medical incident response specialist recording device 534 upon detection of the device 534 within a predetermined proximity to the patient's location as determined from the patient communication device location transponder 522. Thus, as will be appreciated by those of skill in the art, the central server 500 records the video recordings obtained via the medical incident response specialist recording device 534 and the medical incident response station communication device 541 to the medical incident log 503, which provides a complete video record of the patient, the medical incident response specialist and the patient's location during a medical incident, which may be invaluable for purposes of risk mitigation, loss prevention, medical records management, etc.

Once the medical incident response specialist is at the patient's location, he or she will initiate an on-site diagnosis which may be conducted in conjunction with the medical incident specialist and/or the medical incident case manager. More in particular, the medical incident response remains in communication with the medical incident specialist and/or the medical incident case manager via the communicative connection via central server 500 between the medical incident response station communication device 541, the medical incident specialist communication device 514 and/or the medical incident case manager communication device 512. Further, as before, the central server 500 continuously records all communications between the medical incident response station communication device 541, the medical incident specialist communication device 514 and/or the medical incident case manager communication device 512 to the medical incident log 503 throughout the entire medical incident involving the patient.

Upon completion of the on-site diagnosis, the medical incident response specialist instructs the patient regarding the on-site treatment regimen to be implemented, any medications which may be prescribed, and any follow-up activities which the patient is complete on his or her own. Once again, this may be conducted in conjunction with the medical incident specialist and/or the medical incident case manager. Once the onsite medical regimen has been implemented, the medical incident response specialist prepares an electronic medical incident report, as well as a contemporaneous handwritten medical incident report, once again, such as may prove invaluable for purposes of risk mitigation, loss prevention, medical records management, etc.

Figure 16:
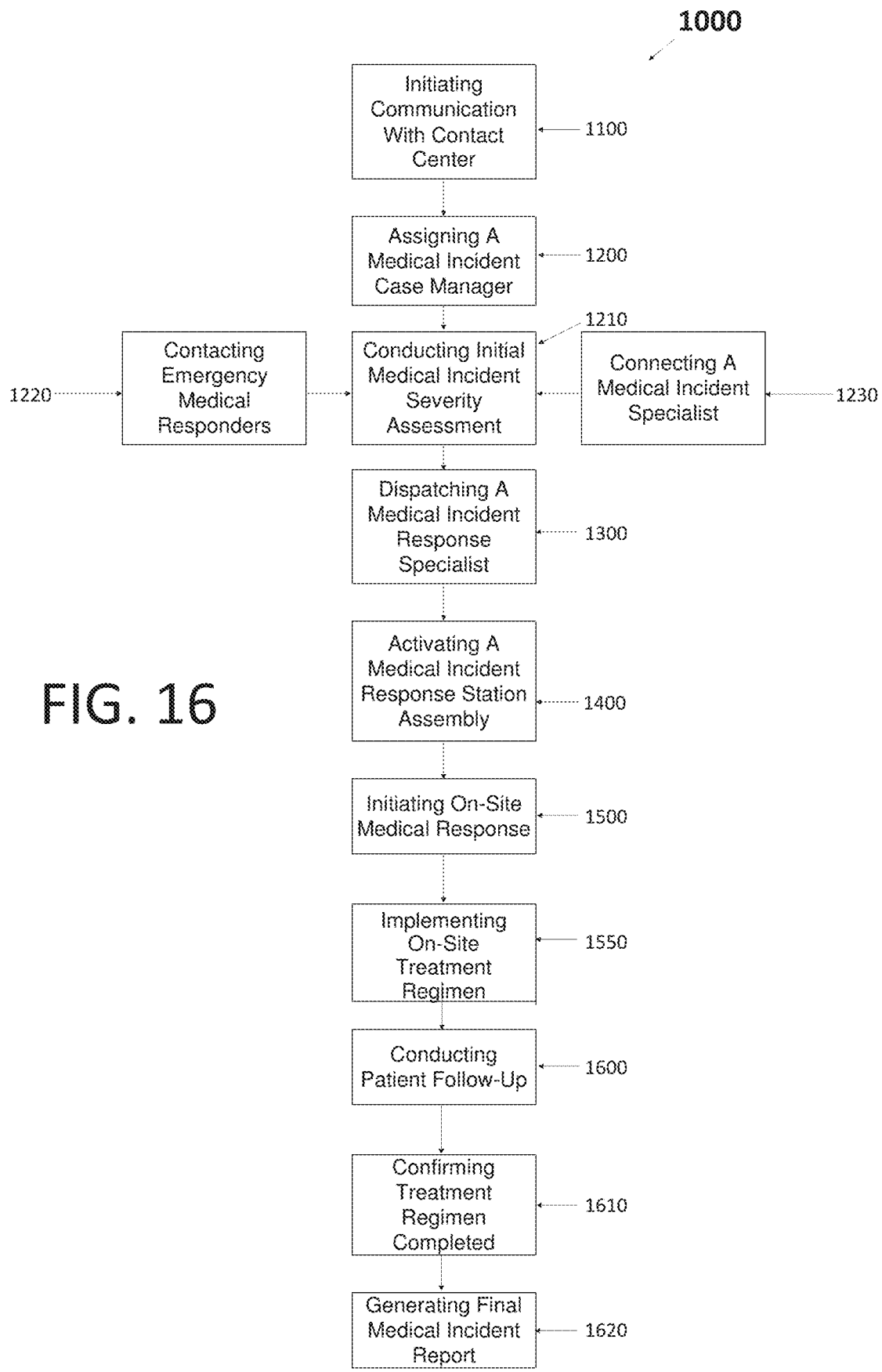
FIG. 16 is one illustrative embodiment of a method for medical incident response and reporting in accordance with the present invention.

FIG. 16 is one illustrative embodiment of a method for medical incident response and reporting 1000 in accordance with the present invention. To begin, the present method for medical incident response and reporting 1000 begins with a patient initiating a medical incident communication with a contact center 1100. As will be appreciated, a patient may utilize a patient communication device, such as disclosed hereinabove, for initiating a medical incident communication with a contact center 1100.

Following a patient initiating a medical incident communication with a contact center 1100, the present method includes a central server actuating a medical incident log module, assigning a unique medical incident identifier and creating a unique medical incident log on a medical incident log module, wherein the central server records all medical incident communications, device locations, treatment regimens and patient follow-up to the unique medical incident log. In at least one embodiment, the present method 1000 further comprises a central server activating a patient communication device location transponder and recording the location of the patient communication device to the unique medical incident log throughout the medical incident involving the patient.

A method for medical incident response and reporting 1000 in accordance with the present invention also includes a central server assigning a medical incident case manager 1200. Once a medical incident case manager has been assigned by a central server, the present method 1000 comprises the central server connecting a medical incident case manager communication device to the patient communication device to facilitate communication between the medical incident case manager and the patient. In at least one embodiment, the present method 1000 includes a central server recording all communications between the medical incident case manager communication device and the patient communication device to the unique medical incident log throughout the medical incident involving the patient.

Turning again to the illustrative embodiment of FIG. 16, a method for medical incident response and reporting 1000 in accordance with the present invention also includes conducting an initial medical incident severity assessment with the patient 1210, typically performed by the medical incident case manager. More in particular, during the initial medical incident severity assessment with the patient, the medical incident case manager must first determine if the patient requires emergency medical treatment. In the event this is the case, the present method 1000, in at least one embodiment, provides for a central server contacting emergency medical responders 1220 proximate to the patient's location. In at least one further embodiment, the present method 1000 further includes a central server contacting an emergency medical facility to alert them as to the patient's condition and estimated time of arrival, and instructing the patient regarding a prescribed emergency medical treatment regimen, such as, via a patient communication device, and confirming with the emergency medical facility that the patient completed the emergency medical treatment regimen.

In the event the medical incident case manager determines that the patient does not require emergency medical treatment, the present method for medical incident response and reporting 1000 in accordance with at least one embodiment of the present invention also includes a central server connecting a medical incident specialist to the patient 1230 via a medical incident specialist communication device to the patient communication device, to facilitate communication between one or more of a medical incident specialist, the medical incident case manager and the patient. The present method 1000 further includes conducting a remote patient diagnosis, and in at least one embodiment, conducting a remote patient diagnosis includes utilizing a portable diagnostic device disposed in a communicative relation with the patient communication device.

In the event the medical incident specialist or the medical incident case manager determines that the patient does not require an on-site medical treatment regimen, the present method 1000 includes instructing patient regarding a self-treatment regimen. This may or may not include prescribing and delivering medication to the patient. Once the self-treatment regimen has been completed, the medical incident specialist or the medical incident case manager attends to preparing electronic medical incident report, as well as a contemporaneous handwritten medical report.

In accordance with at least one embodiment, the present method 1000 further includes a central server recording all communications between the medical incident specialist communication device and the patient communication device to the unique medical incident log throughout the medical incident involving the patient. The present method 1000 also includes, in at least one embodiment, maintaining communication with the patient throughout the medical incident involving the patient.

With reference once again to the illustrative embodiment of FIG. 16, a method for medical incident response and reporting 1000 in accordance with the present invention further comprises a central server dispatching a medical incident response specialist to the patient's location 1300. In at least one embodiment, a central server dispatches a medical incident response specialist via a medical incident response specialist dispatch module. The present method 1000 also includes, in at least one embodiment, maintaining communication with the patient throughout the medical incident involving the patient, such as while a medical incident response specialist has been dispatched and is underway.

With continued reference to the illustrative embodiment of FIG. 16, a method for medical incident response and reporting 1000 also includes a central server activating a medical incident response station assembly 1400. Activating a medical incident response station assembly 1400 in one embodiment includes a central server activating a medical incident response station assembly location transponder, such that the central server can continuously monitor and record the location of the medical incident response station assembly. In at least one further embodiment, activating a medical incident response station assembly 1400 includes a central server conducting a remote inventory of the medical incident response station assembly.

The present method for medical incident response and reporting 1000 in at least some embodiments includes transmitting a location of the medical incident response specialist to the patient until the medical incident response specialist arrives at the patient's location, transmitting the medical incident response specialist's biographical information to patient, including the medical incident response specialist's photograph, transmitting the medical incident response specialist's estimated time of arrival to the patient, transmitting the location of the patient communication device to the medical incident response specialist, and/or transmitting the patient's biographical and medical report to the medical incident response specialist.

Looking once again to the illustrative embodiment of FIG. 16, a method for medical incident response and reporting 1000 in accordance with the present invention further comprises initiating an on-site medical response 1500. In at least one further embodiment, the present method includes a central server activating a medical incident response station communication device and facilitating communications with at least one of the medical incident case manager communication device or the medical incident specialist communication device from the patient's location. As before, the present method also includes a central server recording all communications between the medical incident response station communication device with the medical incident case manager communication device or the medical incident specialist communication device to the unique medical incident log throughout the medical incident involving the patient.

The medical incident response specialist in accordance with at least one embodiment of the present method 1000 is responsible for conducting an on-site diagnosis, which is done in conjunction with communicating with at least one of the medical incident specialists or the medical incident case manager via the medical incident specialist communication device or medical incident case manager communication device, respectively, from the patient's location. In one further embodiment, the present method 1000 also includes instructing the patient regarding an on-site treatment regimen.

Turning once again to the illustrative embodiment of FIG. 16, a method for medical incident response and reporting 1000 in accordance with the present invention also includes implementing the on-site treatment regimen 1550. More in particular, following the on-site diagnosis conducted by the medical incident response specialist while in communication with at least one of the medical incident specialists or the medical incident case manager, an on-site treatment regimen is developed, and that on-site treatment regimen is implemented on the patient by the medical incident response specialist.

Once the on-site treatment regimen has been completed, the present method 1000 includes preparing an electronic medical incident response specialist medical incident report, and in at least one further embodiment, the present method 1000 includes preparing a contemporaneous handwritten medical incident response specialist medical incident report.

The present method for medical incident response and reporting 1000, in accordance with at least one embodiment, further comprises conducting patient follow-up 1600, and in at least one further embodiment, confirming the patient completed the on-site treatment regimen 1610. Once the patient follow-up is completed and confirmation that the patient has completed a treatment regimen, whether it be an emergency treatment regimen, an on-site treatment regimen, or a self-treatment regimen, the present method 1000 includes the central server terminating recording to the unique medical incident log.

With one further reference to the illustrative embodiment of FIG. 16, a method for medical incident response and reporting 1000 in accordance with the present invention comprises a central server generating a final medical incident report. The final medical incident report is based upon and, in at least one embodiment, includes the complete recordings of the communications between the communication devices, the continuously recorded location of various devices as determined from the corresponding location transponders, the complete recording from the medical incident response specialist recording device, and the various electronic medical incident reports as generated by the medical incident case manager, the medical incident specialist, and/or the medical incident response specialist for a particular medical incident involving a patient.

As will be appreciated by the foregoing, a final medical incident report generated by a central server in accordance with either a medical incident response and reporting system 400 or a method for medical incident response and reporting 1000 in accordance with the present invention provides a heretofore unprecedented complete and comprehensive record of a medical incident involving a patient, from the patient's initial communication with a contact center to completion of patient follow-up is completed, including remote and on-site diagnosis, development and implementation of an appropriate treatment regimen, and patient follow-up to assure that a treatment regimen was completed by the patient prior to termination of recording the medical incident to a corresponding and unique medical incident log. As will be appreciated by those of skill in the art, such a final medical incident report may prove invaluable for purposes of risk mitigation, loss prevention, medical records management, etc.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A medical incident response and reporting system comprising:
   a central server including a medical incident log module, and a patient profile module comprising a plurality of patient biographical and medical records,
   a contact center disposed in a communicative relation to said central server, said contact center including at least one medical incident case manager communication device,
   a patient communication device structured to transmit information to a patient's biographical and medical record on said patient profile module via said central server,
   said patient communication device communicative with said at least one medical incident case manager communication device to evaluate medical incidents involving the patient,
   said medical incident case manager communication devices operative to access the patient's biographical and medical records from said patient profile module,
   a medical incident response station assembly transportable to a patient's location and operative to monitor the location of said medical incident response station assembly concurrent to a medical incident involving the patient,
   said medical incident response station assembly further comprising a medical incident response station communication device communicative with said central server to facilitate communication from a patient's location, said central server recording all communications between said medical incident response station communication device and said medical incident case manager communication device to said medical incident log module throughout the medical incident,
   said medical incident log module configured to generate a final medical incident report of a medical incident involving the patient, and
   a recording facility disposed at a location proximate to the patient's location and configured to store at least one recording of the communications between the medical incident response device and the patient.

2. The system as recited in claim 1 wherein said patient communication device comprises a patient communication device location transponder communicative with said central server to continuously monitor the location of said patient communication device throughout a medical incident involving the patient.

3. The system as recited in claim 2 wherein said central server continuously transmits the location of said patient communication device, to said medical incident response specialist communication device concurrent to a medical incident involving the patient.

4. The system as recited in claim 2 comprising said central server recording the location of said patient communication device to said medical incident log module concurrent to a medical incident involving the patient.

5. The system as recited in claim 1 comprising said central server recording communications between said patient communication device and said medical incident specialist communication device to said medical incident log module concurrent to a medical incident involving the patient.

6. The system as recited in claim 1 wherein said medical incident case manager communication device is operative to dispatch the medical incident response assembly to the patient's location via said central server.

7. The system as recited in claim 1 wherein said central server transmits a location of said medical incident response station assembly to said patient communication device until arrival of the medical incident response assembly at a patient's location.

8. The system as recited in claim 1 said central server recording a location of said medical incident response station assembly to said medical incident log module concurrent to a medical incident involving the patient.

9. The system as recited in claim 1 wherein said patient communication device is operable to allow the patient to create the patient's biographical and medical records via said patient profile module.

10. A medical incident response and reporting system comprising:
   a central server including a medical incident log module, a medical incident specialist contact module, a medical incident response specialist dispatch module, and a patient profile module comprising a plurality of patient biographical and medical records,
   a contact center disposed in a communicative relation to said central server, said contact center including a plurality of medical incident case manager communication devices,
   a patient communication device structured to transmit information to a patient's biographical and medical record on said patient profile module via said central server,
   said patient communication device communicative with said plurality of medical incident case manager communication devices communicative between the patient and the medical incident case manager device to evaluate a medical incident involving the patient,
   said patient communication device operative to monitor a location of said patient communication device, said central server recording a location of said patient communication device to said medical incident log module concurrent a medical incident involving the patient,
   said medical incident case manager communication device operative to access the patient's biographical and medical records from said patient profile module,
   a medical incident response station assembly transportable to a patient's location and equipped with a plurality of preselected medical implements each comprising a radio frequency identification tag,
   said medical incident response station assembly communicative with said central server to monitor the location of said medical incident response station assembly,
   said medical incident response station assembly further comprising a medical incident response station communication device operative to communicate between at least the patient, the medical incident response station assembly, from a patient's location,
   a medical incident response specialist recording device activated upon arrival of the medical incident response station assembly to the patient's location and communicative with said medical incident log module,
   said medical incident response specialist recording device recording the environment surrounding the medical incident response from the arrival of the medical incident response station assembly to a patient's location until departure of the medical incident response station assembly from a patient's location,
   said medical incident log module configured to generate a final medical incident report of the medical incident involving the patient; and
   a recording facility disposed at a location proximate to the patient's location and configured to store at least one recording of the communications between the medical incident response device and the patient.

11. The system as recited in claim 10 further comprising a portable diagnostic device operable by the patient and communicative with said patient communication device.

12. The system as recited in claim 11 wherein said portable diagnostic device transmits a plurality of diagnostic parameters to said central server via said patient communication device for access by at least one of a medical incident case manager or a medical incident specialist.

13. The system as recited in claim 12 wherein said central server is operative to record said plurality of diagnostic parameters to said medical incident log module.

14. The system as recited in claim 13 wherein at least one of said plurality of preselected medical implements comprises a medical instrument.

15. The system as recited in claim 13 wherein at least one of said plurality of preselected medical implements comprises a medical supply.

16. The system as recited in claim 13 wherein at least one of said plurality of preselected medical implements comprises a medication.

\* \* \* \* \*